US007666876B2

(12) United States Patent
Birch et al.

(10) Patent No.: US 7,666,876 B2
(45) Date of Patent: *Feb. 23, 2010

(54) BUPRENORPHINE FORMULATIONS FOR INTRANASAL DELIVERY

(75) Inventors: Phillip John Birch, Cambridge (GB); Ann Gail Hayes, Cambridge (GB); Peter James Watts, Nottingham (GB); Jonathan David Castile, Nottingham (GB)

(73) Assignees: Vernalis (R&D) Limited, Winnersh, Berkshire (GB); Archimedes Development Limited, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/508,336

(22) PCT Filed: Mar. 19, 2002

(86) PCT No.: PCT/GB03/01183

§ 371 (c)(1),
(2), (4) Date: Dec. 1, 2004

(87) PCT Pub. No.: WO03/080021

PCT Pub. Date: Oct. 2, 2003

(65) Prior Publication Data

US 2005/0085440 A1 Apr. 21, 2005

(30) Foreign Application Priority Data

| Mar. 19, 2002 | (GB) | .................................. 0206448.3 |
| Oct. 28, 2002 | (GB) | .................................. 0225040.5 |
| Oct. 28, 2002 | (GB) | .................................. 0225041.3 |
| Oct. 28, 2002 | (GB) | .................................. 0225042.1 |

(51) Int. Cl.
A01N 43/42 (2006.01)
A61K 31/35 (2006.01)
A61K 31/715 (2006.01)
A61F 13/00 (2006.01)
C07D 498/00 (2006.01)
C07D 513/00 (2006.01)
C07D 515/00 (2006.01)

(52) U.S. Cl. .................... 514/282; 514/54; 514/453; 424/434; 546/44

(58) Field of Classification Search ................ 424/400, 424/434; 514/279, 282, 54, 453; 546/44
See application file for complete search history.

(56) References Cited

U.S. PATENT DOCUMENTS

| 4,981,875 A | 1/1991 | Leusner et al. |
| 5,147,648 A | 9/1992 | Bannert |
| 5,456,745 A | 10/1995 | Roreger et al. |
| 5,508,042 A | 4/1996 | Oshlack et al. |
| 6,090,368 A | 7/2000 | Zin et al. |
| 6,387,917 B1 * | 5/2002 | Illum et al. .................. 514/282 |
| 6,432,440 B1 | 8/2002 | Watts et al. |
| 6,610,271 B2 | 8/2003 | Wermeling |
| 6,777,000 B2 * | 8/2004 | Ni et al. ...................... 424/488 |
| 2003/0077300 A1 | 4/2003 | Wermeling |
| 2005/0142072 A1 | 6/2005 | Birch et al. |
| 2007/0231269 A1 | 10/2007 | Birch et al. |

FOREIGN PATENT DOCUMENTS

| EP | 0 460 020 B1 | 9/1990 |
| EP | 0 571 671 A1 * | 1/1993 |
| EP | 0 571 671 A | 12/1993 |
| EP | 1 108 423 A1 | 6/2001 |
| GB | 2 378 383 A | 2/2003 |
| JP | 7-503481 | 4/1995 |
| JP | 2000-229859 | 8/2000 |
| JP | 2000 229859 A | 8/2000 |
| JP | 2001-2589 | 1/2001 |
| JP | 2001-524094 | 11/2001 |
| WO | 82/03768 | 11/1982 |
| WO | WO 87/04350 | 7/1987 |
| WO | WO 88/10121 | 12/1988 |
| WO | 90/09780 | 9/1990 |
| WO | 93/15737 A | 8/1993 |
| WO | WO 94/10987 | 5/1994 |
| WO | WO 96/33694 | 10/1996 |
| WO | WO 97/04780 | 2/1997 |
| WO | 98/47535 A | 10/1998 |
| WO | WO 98/47535 | * 10/1998 |

(Continued)

OTHER PUBLICATIONS

Eriksen, J. et al. J. Pharm. Pharmacol. 1989, 41, 803-805.*
Reich, I., et al. "Tonicity, Osmoticity, Osmolality and Osmolarity" Remington: The Science and Practice or Pharmacv, Nineteenth Edition, vol. 1. Easton, PA: Mack, 1995. pp. 613-615.*

(Continued)

Primary Examiner—Sreeni Padmanabhan
Assistant Examiner—Umamaheswari Ramachandran
(74) Attorney, Agent, or Firm—Nixon & Vanderhye P.C.

(57) ABSTRACT

Aqueous formulations suitable for intranasal administration comprise buprenorphine or a physiologically acceptable salt or ester thereof and (a) a pectin having a degree of esterification of less than 50%, (b) chitosan and a polyoxyethylene-polyoxypropylene copolymer (poloxamer) or (c) chitosan and hydroxypropylmethylcellulose. Such formulations can induce rapid and prolonged analgesia when delivered intranasally to a patient. The buprenorphine or buprenorphine salt or ester may be delivered to the bloodstream to produce within 30 minutes a therapeutic plasma concentration of buprenorphine, $C_{ther}$, of 0.2 ng/ml or greater which is maintained for a duration $T_{maint}$ of at least 2 hours.

26 Claims, 2 Drawing Sheets

FOREIGN PATENT DOCUMENTS

| WO | 99/09962 A | 3/1999 |
|---|---|---|
| WO | WO 99/13799 | 3/1999 |
| WO | 99/27905 A | 6/1999 |
| WO | WO 99/45963 | 9/1999 |
| WO | WO 00/12063 | 3/2000 |
| WO | 01/29046 A | 4/2001 |
| WO | 01/035942 A3 | 5/2001 |
| WO | WO 01/58447 A1 | 8/2001 |
| WO | 02/00195 A | 1/2002 |
| WO | WO 02/00195 * | 1/2002 |
| WO | 02/067897 A | 9/2002 |
| WO | WO 03/080022 A2 | 10/2003 |

OTHER PUBLICATIONS

Nairn, J. G. Solutions, Emulsions, Suspensions and Extracts Remington: The Science and Practice or Pharmacv, Nineteenth Edition, vol. 2. Easton, PA: Mack, 1995. p. 1502.*

Eriksen et al; "The Systemic Availability of Buprenorphine Administered by Nasal Spray"; J. Pharm. Pharmacol., 1989, 41: 803-805, Apr. 13, 1989.

Cassidy et al; "Controlled Buccal Delivery of Buprenorphine"; Journal of Controlled Release, vol. 25, 1993, pp. 21-29.

Reynolds; Martindale, The Extra Pharmacopoeia, Thirty-first Edition, 1996, pp. 43-45.

Semde et al, "Leaching of pectin from mixed pectin/insoluble polymer films intended for colonic drug delivery", International Journal of Pharmaceutics 174 (1998) 233-241.

Hussain et al, "Nasal absorption of naloxone and buprenorphine in rats", International Journal of Pharmaceutics, 21 (1984) 233-237.

International Journal of Pharmaceutics, 129, 1996, 233-239 (Talukdar et al).

International Journal of Pharmaceutics, 217, 2001, 121-126 (Lindhardt et al).

International Journal of Pharmaceutics, 205, 2000, 159-163 (Lindhardt et al).

Merck Index, 13$^{th}$ edition, 2001, Entry 6551.

Verma et al, J. Psychol. Pharmacol., vol. 7, No. 3, pp. 270-275, 1993.

Soane et al, Int. J. Pharm., 178, 55-65, 1999.

Machine English translation of JP 2000-229859 as well as a partial English language translation.

* cited by examiner

BUPRENORPHINE FORMULATIONS FOR INTRANASAL DELIVERY

This application is the U.S. national phase of international application PCT/GB03/01183, filed 19 Mar. 2003, which designated the U.S. and claims priority to GB Application No. 0206448.3 filed 19 Mar. 2002, GB Application No. 0225040.5 filed 28 Oct. 2002, GB 0225041.3 filed 28 Oct. 2002 and GB Application No. 0225042.1 filed 28 Oct. 2002. The entire contents of these applications are incorporated herein by reference.

FIELD OF THE INVENTION

The invention relates to pharmaceutical formulations of buprenorphine and physiologically acceptable salts and esters thereof.

BACKGROUND OF THE INVENTION

The term opioid (or opiate) defines drugs with morphine-like properties. Opioids can be sub-classified on the basis of their receptor specificity. Mu-agonist opioids provide intense analgesia. These opioids can be long-acting (e.g. methadone) or short-acting (e.g. remifentanil).

Mixed agonist/antagonist opioids (e.g. butorphanol and buprenorphine) are partial agonists (the former at mu and kappa receptors and the latter at the mu receptor) and can produce good quality analgesia. They produce less respiratory depression and constipation than high efficacy mu agonists.

Buprenorphine (CAS RN 52485-79-7; [5α,7α(S)-17-(Cyclopropylmethyl)-α-(1,1-dimethylethyl)-4,5-epoxy-18,19-dihydro-3-hydroxy-6-methoxy-α-methyl-6,14-ethenomorphinan-7-methanol) has the formula:

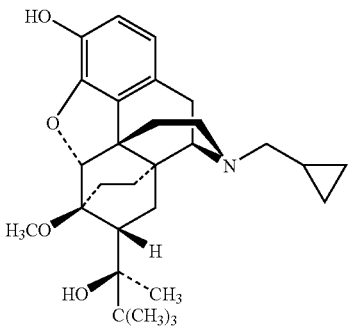

The hydrochloride is also active (CAS RN 53152-21-9).

Buprenorphine is a highly lipophilic derivative of thebaine. It is a partial mu agonist and mediates analgesia at the mu opioid receptor. Buprenorphine produces a similar maximum analgesic effect to full mu agonists such as morphine in animal models of pain and, although it may have a ceiling effect in certain pain types in man, it has been shown to produce good quality analgesia of similar efficacy to morphine in most clinical situations including severe pain. An unusual property of buprenorphine observed in in vitro studies is its very slow rate of dissociation from its receptor.

As a class, opioids are associated with a number of undesirable side-effects, including respiratory depression, nausea, vomiting, dizziness, mental clouding, dysphoria, pruritus, constipation, increased biliary tract pressure, urinary retention and hypotension. The development of tolerance and the risk of chemical dependence and abuse are further problems. Buprenorphine, however, is unusual in exhibiting a low maximum effect for respiratory depression and also a bell-shaped dose response curve where the effect first increases with larger doses, reaches a ceiling and then diminishes as the dosage is further increased, which makes it a safer drug than morphine, where respiratory depression will ultimately lead to death. Buprenorphine has also been shown to have a lower incidence of other side-effects like constipation in man, and it has a lower abuse potential than full mu agonists.

Buprenorphine has previously been administered via the intravenous, intramuscular and sublingual routes to human subjects. There are limited reports of nasal administration. Eriksen et al, J. Pharm. Pharmacol. 41, 803-805, 1989 report administration to human volunteers of a nasal spray. The spray consisted of 2 mg/ml of buprenorphine hydrochloride dissolved in 5% dextrose and the pH of the solution was adjusted to pH 5.

WO 90/09870 describes a composition for administration to mucosa comprising a pharmacologically active compound and a polycationic substance such as DEAE-dextran or chitosan. WO 98/47535 discloses a single component liquid pharmaceutical composition for administration to a mucosal surface. The composition comprises a therapeutic agent, a pectin with a low degree of esterification and an aqueous carrier that gels or can be adapted to gel at the site of application. Neither WO 90/09780 nor WO 98/47535 mentions buprenorphine.

SUMMARY OF THE INVENTION

Improved buprenorphine formulations for nasal administration have now been devised. Rapid uptake of the buprenorphine across the nasal mucosa into the plasma can be achieved, which results in fast onset of analgesia. Further, the residence time of the buprenorphine in the nasal cavity can be increased, which results in prolonged analgesia. An improved profile of absorption of buprenorphine into the systemic circulation can thus be achieved by use of the formulation.

Accordingly, the present invention provides:

(1) an aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%; which solution has a pH of from 3 to 4.2, is substantially free from divalent metal ions and gels on the nasal mucosa;

(2) an aqueous solution suitable for intranasal administration, which comprises:
  (a) from 0.1 to 10 mg/ml of buprenorphine or a physiologically acceptable salt or ester thereof,
  (b) from 0.1 to 20 mg/ml of a chitosan, and
  (c) from 0.1 to 15 mg/ml of hydroxypropylmethylcellulose (HPMC);
  which solution has a pH of from 3 to 4.8; and (3) an aqueous solution suitable for intranasal administration, which comprises:
  (a) from 0.1 to 10 mg/ml of buprenorphine or a physiologically acceptable salt or ester thereof,
  (b) from 0.1 to 20 mg/ml of a chitosan, and
  (c) from 50 to 200 mg/ml of a polyoxyethylene-polyoxypropylene copolymer of the general formula $HO(C_2H_4O)_a(C_3H_6O)_b(C_2H_4O)_aH$ wherein a is from 2 to 130 and b is from 15 to 67;
  which solution has a pH of from 3 to 4.8.

A preferred solution of the invention has a pH of from 3.5 to 4.0, is substantially free from divalent metal ions and comprises:
(a) from 1 to 6 mg/ml of buprenorphine or a physiologically acceptable salt or ester thereof, calculated as buprenorphine,
(b) from 10 to 40 mg/ml of a pectin which has a degree of esterification from 10 to 35%, and
(c) dextrose as a tonicity adjustment agent.

The invention also provides:

a process for the preparation of solution (1), which comprises dissolving buprenorphine or a physiologically acceptable salt or ester thereof in water; mixing the resulting solution with a solution in water of a pectin having a degree of esterification of less than 50% such that the mixed solution comprises from 0.1 to 10 mg/ml of buprenorphine or said salt or ester thereof and from 5 to 40 mg/ml of the pectin; and adjusting the pH of the solution to a value from 3 to 4.2 if desired;

a process for the preparation of solution (2), which comprises dissolving buprenorphine or a physiologically acceptable salt or ester thereof, a chitosan and HPMC in water to provide a solution comprising from 0.1 to 10 mg/ml of buprenorphine or said salt or ester thereof, from 0.1 to 20 mg/ml of chitosan and from 0.1 to 15 mg/ml of HPMC; and adjusting the pH of the solution to a value from 3 to 4.8 as desired;

a process for the preparation of solution (3), which comprises dissolving buprenorphine or a physiologically acceptable salt or ester thereof, a chitosan and a polyoxyethylene-polyoxypropylene copolymer of the general formula $HO(C_2H_4O)_a(C_3H_6O)_b(C_2H_4O)_aH$ wherein a is from 2 to 130 and b is from 15 to 67, in water to provide a solution comprising from 0.1 to 10 mg/ml of buprenorphine or said salt or ester thereof, from 0.1 to 20 mg/ml of a chitosan and from 50 to 200 mg/ml of the polyoxyethylene-polyoxypropylene copolymer; and adjusting the pH of the solution to a value from 3 to 4.8 as desired;

a nasal delivery device loaded with a solution of the invention;

use of a solution of the invention for the manufacture of a nasal delivery device for use in inducing analgesia; and a method of inducing analgesia in a patient in need thereof, which method comprises intranasally administering a solution of the invention to the patient.

The invention enables a therapeutic blood plasma concentration of buprenorphine, i.e. a buprenorphine concentration that produces pain relief or pain amelioration, to be attained within 30 minutes and maintained for up to 24 hours. The term $C_{ther}$ denotes a therapeutic blood plasma concentration. The term $T_{maint}$ denotes the duration for which $C_{ther}$ is maintained.

Additionally, therefore, the present invention provides use of buprenorphine or a physiologically acceptable salt or ester thereof and a delivery agent for the manufacture of a medicament for administration intranasally for the treatment of pain whereby, on introduction into the nasal cavity of a patient to be treated, the buprenorphine or salt or ester thereof is delivered to the bloodstream to produce within 30 minutes a therapeutic plasma concentration $C_{ther}$ of 0.2 ng/ml or greater which is maintained for a duration $T_{maint}$ of at least 2 hours.

Also provided are:

use of a pharmaceutical composition which comprises buprenorphine or a physiologically acceptable salt or ester thereof and a delivery agent for the manufacture of a nasal delivery device for use in inducing analgesia whereby, on introduction into the nasal cavity of a patient to be treated, the buprenorphine or salt or ester thereof is delivered to the bloodstream to produce within 30 minutes a therapeutic plasma concentration $C_{ther}$ of 0.2 ng/ml or greater which is maintained for a duration $T_{maint}$ of at least 2 hours;

a pharmaceutical composition suitable for use as an analgesic which comprises buprenorphine or a physiologically acceptable salt or ester thereof and a delivery agent whereby, on introduction into the nasal cavity of a patient to be treated, the buprenorphine or salt or ester thereof is delivered to the bloodstream to produce within 30 minutes a therapeutic plasma concentration $C_{ther}$ of 0.2 ng/ml or greater which is maintained for a duration $T_{maint}$ of at least 2 hours;

a method of inducing analgesia in a patient in need thereof, which method comprises administering intranasally to said patient a pharmaceutical composition which comprises buprenorphine or a physiologically acceptable salt or ester thereof and a delivery agent whereby, on introduction into the nasal cavity of said patient to be treated, the buprenorphine or salt or ester thereof is delivered to the bloodstream to produce within 30 minutes a therapeutic plasma concentration $C_{ther}$ of 0.2 ng/ml or greater which is maintained for a duration $T_{maint}$ of at least 2 hours.

DETAILED DESCRIPTION OF THE INVENTION

Figure 1:
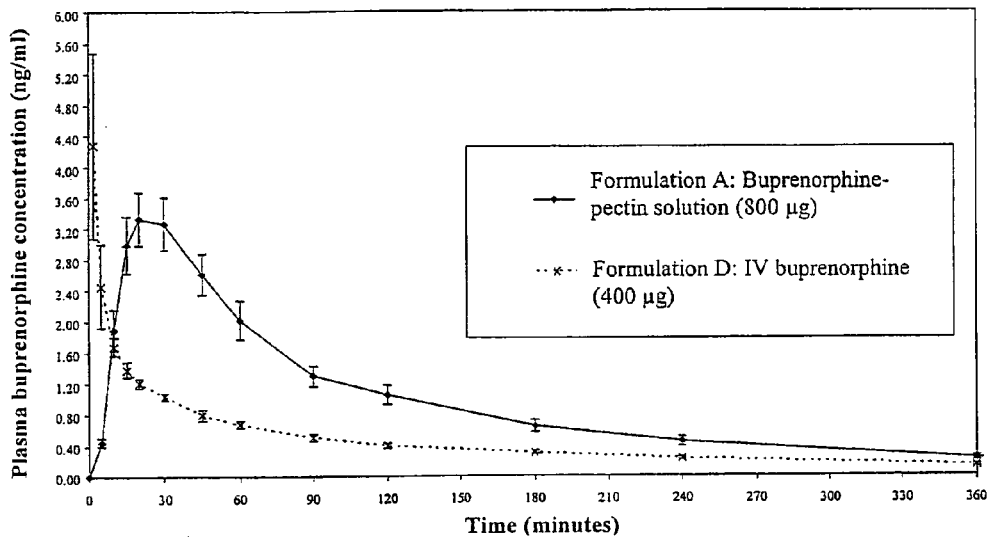
FIGS. 1 to 3 show the pharmacokinetic profiles that were obtained when buprenorphine formulations according to the invention (Formulations A to C) were administered intranasally to healthy volunteers at a dose of 800 µg of buprenorphine hydrochloride, calculated as buprenorphine. Formulation A: buprenorphine hydrochloride-pectin solution. Formulation B: buprenorphine hydrochloride-chitosan/hydroxypropylmethylcellulose (HPMC) solution. Formulation C: buprenorphine hydrochloride-chitosan/poloxamer 188 solution. Also shown for comparison is the pharmacokinetic profile that was obtained when a commercial solution of buprenorphine hydrochloride (Temgesic—trade mark; Formulation D) was administered intravenously to healthy volunteers in the same study at a dose of 400 µg of buprenorphine hydrochloride, calculated as buprenorphine.

A first pharmaceutical solution of the invention consists essentially of 0.1 to 10 mg/ml of buprenorphine or a physiologically acceptable salt or ester thereof, from to 40 mg/ml of a pectin having a low degree of esterification, in particular a degree of esterification of less than 50%, and water. The buprenorphine salt may be an acid addition salt or a salt with a base. Suitable acid addition salts include the hydrochloride, sulphate, methane sulphonate, stearate, tartrate and lactate salts. The hydrochloride salt is preferred.

The concentration of buprenorphine or buprenorphine salt or ester is from 0.1 to 10 mg/ml, for example from 0.5 to 8 mg/ml. Preferred concentrations are 1 to 6 mg/ml, for example 1 to 4 mg/ml calculated as buprenorphine. Suitable solutions can contain buprenorphine or a buprenorphine salt or ester in an amount of 1 mg/ml or 4 mg/ml, calculated as buprenorphine.

The solution is typically delivered as a nasal spray. A 100 µl spray of a solution containing 1 to 4 mg/ml of buprenorphine or a buprenorphine salt or ester, calculated as buprenorphine thus results in a clinical dose of 100 to 400 μg of the buprenorphine or buprenorphine salt or ester, calculated as buprenorphine. Two such sprays may be given per nostril per administration time to deliver a dose of up to 4×400 μg, i.e. up to 1600 μg, of buprenorphine or the buprenorphine salt or ester, calculated as buprenorphine.

The pectin is a gelling agent. The solution of the invention gels on the mucosal surfaces of the nasal cavity after delivery without the need for an extraneous source of divalent metal ions. The buprenorphine or buprenorphine salt or ester that is formulated with the pectin is thus retained for longer on the surfaces of the nasal epithelium. The resulting sustained release of the buprenorphine or buprenorphine salt or ester into the bloodstream enables prolonged analgesia to be achieved. Improved delivery of buprenorphine or a buprenorphine salt or ester can consequently be obtained. Rapid uptake of the buprenorphine or buprenorphine salt or ester also results, which leads to fast onset of analgesia.

The solutions of the invention contain a pectin having a degree of esterification of less than 50%. A pectin is a polysaccharide substance present in the cell walls of all plant tissues. Commercially pectins are generally obtained from the dilute acid extract of the inner portion of the rind of citrus fruits or from apple pomace. A pectin consists of partially methoxylated polygalacturonic acids. The proportion of galacturonic acid moieties in the methyl ester form represents the degree of esterification (DE). The term DE is well understood by those skilled in the art and may be represented as the percentage of the total number of carboxyl groups that are esterified, i.e. if four out of five acid groups is esterified this represents a degree of esterification of 80%, or as the methoxyl content of the pectin. DE as used herein refers to the total percentage of carboxyl groups that are esterified. Pectins can be categorised into those having a low degree of esterification (low methoxylation) or a high degree of esterification (high methoxylation). A "low DE" or "LM" pectin has a degree of esterification below 50% whereas a "high DE" or "HM" pectin has a degree of esterification of 50% or above. The gelling properties of aqueous pectin solutions can be controlled by the concentration of pectin, the type of pectin, especially the degree of esterification of the galacturonic acid units, and the presence of added salts.

Low DE pectins are used in the present invention. The primary mechanism by which such pectins gel in aqueous solution is through exposure to metal ions, such as those found in the nasal mucosal fluid as described in WO 98/47535. The degree of esterification of the pectin used in the invention is preferably less than 35%. The degree of esterification may thus be from 10 to 35%, for example from 15 to 25%. Low DE pectins may be purchased commercially. An example of a low DE pectin is SLENDID (trade mark) 100, supplied by CP Kelco (Lille Skenved) which has a degree of esterification of around 15 to 25%.

A pectin-containing solution of the invention must not gel on storage. It should not gel prior to application to the nasal cavity. It must therefore be substantially free of agents which would cause the solution to gel. In particular, a solution of the invention must be substantially free of divalent metal ions and especially calcium ions. The content of divalent metal ions in the solution must therefore be minimised. A solution of the invention may therefore contain a negligible concentration of divalent metal ions or there may no detectable divalent metal ions.

A pectin is present in the solutions of the invention at a concentration of from 5 to 40 mg/ml, for example from 5 to 30 mg/ml. More preferably, the pectin concentration is from 10 to 30 mg/ml or from 10 to 25 mg/ml. The pectin and the pectin concentration are selected such that the solution gels on delivery to the nasal mucosa. The solution gels on the nasal mucosa in the absence of an extraneous source of divalent metal ions, e.g. $Ca^{2+}$ ions.

A pectin-containing solution of the invention has a pH of from 3 to 4.2. Any pH within this range may be employed provided the buprenorphine or buprenorphine salt or ester-emains dissolved in the solution. The pH may be from 3.2 to 4.0, for example from 3.5 to 4.0. A particularly suitable pH is from 3.6 to 3.8. The pH may be adjusted to an appropriate value by addition of a physiologically acceptable acid and/or physiologically acceptable buffer. The pH may thus be adjusted solely by means of a physiologically acceptable mineral acid or solely by means of a physiologically acceptable organic acid. The use of hydrochloric acid is preferred.

Any suitable preservative may be present in the solution, in particular a preservative that prevents microbial spoilage of the solution. The preservative may be any pharmaceutically acceptable preservative, for example phenylethyl alcohol or propyl hydroxybenzoate (propylparaben) or one of its salts. The phenylethyl alcohol and the propylparaben or propylparaben salt are preferably used in combination. The preservative must be compatible with the other components of the solution and, in particular, must not cause gelling of the solution.

Solutions may include a tonicity adjustment agent such as a sugar, for example dextrose, or a polyhydric alcohol for example mannitol. A solution may be hypertonic, substantially isotonic or hypotonic. A substantially isotonic solution can have an osmolality of from 0.28 to 0.32 osmol/kg. An exactly isotonic solution is 0.29 osmol/kg. The osmolality of the solution may be from 0.1 to 0.8 osmol/kg such as from 0.2 to 0.6 osmol/kg or preferably from 0.3 to 0.5 osmo/kg. A sufficient amount of a tonicity adjustment agent such as dextrose or mannitol may therefore be present to achieve such osmolalities. Preferably a solution contains 50 mg/ml dextrose or mannitol.

A pectin-containing solution of the invention is prepared by dissolving buprenorphine or a physiologically acceptable salt or ester thereof in water, typically Water for Injections, and the resulting solution is mixed with a solution of a suitable pectin in water, again typically Water for Injections. The amount of the buprenorphine or salt or ester thereof and of the pectin are selected so that from 0.1 to 10 mg/ml of buprenorphine or the buprenorphine salt or ester and from 5 to 40 mg/ml of pectin are dissolved in the mixed solution. A preservative or combination of preservatives may be dissolved in the solution. The pH of the mixed solution can be adjusted to a value within the range from 3 to 4.2 as required. Preferably, the pH is adjusted with hydrochloric acid if pH adjustment is required.

Other components can be provided in solution at any convenient stage. For example, dextrose or mannitol may be dissolved in the water in which the buprenorphine or buprenorphine salt or ester is being dissolved. A sterile solution can be obtained either by using sterile starting materials and operating under sterile conditions and/or by using standard sterilising techniques such as passing the final solution through a sterilising filter. A pyrogen-free solution can thus be provided. The solution can then be introduced into a nasal delivery device, typically a sterile such device. If required, prior to sealing the device, the solution may be overlaid with an inert gas such as nitrogen to protect it from oxidation.

A second solution of the invention consists essentially of 0.1 to 10 mg/ml of buprenorphine or a physiologically acceptable salt or ester thereof, from 0.1 to 20 mg/ml of a chitosan, from 0.1 to 15 mg/ml of HPMC, and water. A third solution of the invention consists essentially of 0.1 to 10 mg/ml of buprenorphine or a physiologically acceptable salt or ester thereof, from 0.1 to 20 mg/ml of chitosan, from 50 to 200 mg/ml of a polyoxyethylene-polyoxypropylene copolymer of the general formula $HO(C_2H_4O)_a(C_3H_6O)_b(C_2H_4O)_aH$ wherein a is from 2 to 130 and b is from 15 to 67, and water.

In each case, the buprenorphine salt may be an acid addition salt or a salt with a base. Suitable acid addition salts are mentioned above. They include the hydrochloride, sulphate, methane sulphonate, stearate, tartrate and lactate salts. The hydrochloride salt is preferred.

The concentration of buprenorphine or buprenorphine salt or ester in either solution is from 0.1 to 10 mg/ml, for example from 0.5 to 8 mg/ml. Preferred concentrations are 1 to 6 mg/ml, for example 1 to 4 mg/ml. Suitable solutions can contain the buprenorphine or buprenorphine salt or ester at a concentration of 1 mg/ml or 4 mg/ml, calculated as buprenorphine. Each solution is typically delivered as a nasal spray. A 100 μl spray of a solution containing 1 to 4 mg/ml of buprenorphine or a buprenorphine salt or ester, calculated as buprenorphine, thus results in a clinical dose of 100 to 400 μg of the buprenorphine or buprenorphine salt or ester, calculated as buprenorphine. Two such sprays may be given per nostril per administration time to deliver a dose of up to 4×400 μg, i.e. up to 1600 μg, of buprenorphine or the buprenorphine salt or ester, calculated as buprenorphine.

A chitosan is present in both solutions. Chitosans are cationic polymers that have mucoadhesive properties. The mucoadhesion is thought to result from an interaction between the positively charged chitosan molecule and the negatively charged sialic acid groups on mucin (Soane et al, Int. J. Pharm 178, 55-65, 1999).

By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). Preferably, the chitosan is produced from chitin by deacetylation to a degree of greater than 40%, preferably between 50 and 98%, more preferably between 70% and 90%.

The chitosan typically has a molecular weight of 4,000 Da or more, preferably from 10,000 to 1,000,000 Da, more preferably from 15,000 to 750,000 Da and most preferably from 50,000 to 500,000 Da.

The chitosan may thus be a deacetylated chitin. It may be a physiologically acceptable salt. Suitable physiologically acceptable salts include salts with a pharmaceutically acceptable mineral or organic acid such as the nitrate, phosphate, lactate, citrate, hydrochloride and acetate salts. Preferred salts are chitosan glutmate and chitosan hydrochloride.

The chitosan may be a derivative of a deacetylated chitin. Suitable derivatives include, but are not limited to, ester, ether or other derivatives formed by bonding of acyl and/or alkyl groups with the hydroxy groups, but not the amino groups, of a deacetylated chitin. Examples are $O-(C_1-C_6$ alkyl) ethers of deacetylated chitin and O-acyl esters of deacetylated chitin. Derivatives also include modified forms of a deacetylated chitin for example a deacetylated chitin conjugated to polyethylene glycol.

Low and medium viscosity chitosans suitable for use in the present invention may be obtained from various sources, including FMC Biopolymer, Drammen, Norway; Seigagaku America Inc., MD, USA; Meron (India) Pvt, Ltd., India; Vanson Ltd, VA, USA; and AMS Biotechnology Ltd., UK. Suitable derivatives include those that are disclosed in Roberts, Chitin Chemistry, MacMillan Press Ltd., London (1992). Particularly preferred chitosan compounds that may be mentioned include "Protosan"(trade mark) available from FMC Biopolymer, Drammen, Norway. The chitosan is preferably water-soluble.

An aqueous solution of chitosan may be prepared by dissolving chitosan base or a derivative of chitosan base in a pharmaceutically acceptable mineral or organic acid such as hydrochloric, lactic, citric or glutamic acid or by dissolving a chitosan salt in water.

The chitosan is present in solution at a concentration of from 0.1 to 20 mg/ml, for example from 0.5 to 20 mg/ml. Preferably the solution contains from 1 to 15 mg/ml, more preferably from 2 to 10 mg/ml, of chitosan. A chitosan concentration of 5 mg/ml is particularly suitable.

Any suitable hydroxypropylmethylcellulose (HPMC) may be employed. Several grades of HPMC are available. For example, Dow Chemical Company produces a range of HPMC polymers under the trade mark Methocel. The grade and concentration of HPMC is chosen such that the solution of the invention preferably has a viscosity, at 25° C. as measured by a cone and plate viscometer (e.g. Brookfield), in the range from 1 to 200 cps, more preferably from 3 to 150 cps and most preferably from 5 to 100 cps.

Producing a solution having a particular viscosity is within the capability of one skilled in the at and can be achieved, for example, by using a high concentration of a low viscosity HPMC or a low concentration of a high viscosity HPMC. The HPMC used in the solution of the invention is preferably one having an apparent viscosity (measured as a 2% solution in water at 20° C.) in the range from 3000 to 6000 cps. The concentration of the HPMC having a viscosity of from 3000 to 6000 cps is in the range from 0.1 to 15 mg/ml, preferably from 0.5 to 10 mg/ml and preferably from 1 to 5 mg/ml.

The polyoxyethylene-polyoxypropylene copolymer typically has a molecular weight of from 2,500 to 18,000 for example from 7,000 to 15,000. The copolymer is a block copolymer of the general formula

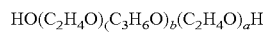

wherein a is from 2 to 130 and b is from 15 to 67. The value for a may be from 40 to 100 such as from 60 to 90 or from 70 to 95. The value for b may be from 20 to 40 such as from 25 to 35.

Such copolymers are known as poloxamers. Several different types of poloxamer are available commercially, from suppliers such as BASF, and vary with respect to molecular weight and the proportions of ethylene oxide "a" units and propylene oxide "b" units. A commercially available poloxamer suitable for use in the present invention is poloxamer 188 which structurally contains 80 "a" units and 27 "b" units and has a molecular weight of 7680-9510 (Handbook of Pharmaceutical Excipients, editor A. H. Kippe, third edition, Pharmaceutical Press, London, UK, 2000). Preferably the poloxamer is poloxamer 188.

When the solutions contain a poloxamer, the poloxamer is present at a concentration in the range of from 50 to 200 mg/ml, preferably from 65 to 160 mg/ml and more preferably from 80 to 120 mg/ml. A preferred concentration is 100 mg/ml.

Any suitable preservative may be present in the solution, in particular a preservative that prevents microbial spoilage of the solution. The preservative must be compatible with the other components of the solution. The preservative may be any pharmaceutically acceptable preservative, for example a quaternary ammonium compound such as benzalkonium chloride.

The solution has a pH of from 3 to 4.8. Any pH within this range may be employed provided the buprenorphine or buprenorphine salt or ester remains dissolved in the solution. The pH may be from 3.2 to 4.2, for example from 3.2 to 4.0 or 3.5 to 4.0. A particularly suitable pH is from 3.6 to 3.8. The pH may be adjusted to an appropriate value by addition of a physiologically acceptable acid and/or physiologically acceptable buffer. The pH may thus be adjusted solely by means of a physiologically acceptable mineral acid or solely by means of a physiologically acceptable organic acid. The use of hydrochloric acid is preferred.

A tonicity adjustment agent may be included in the solution. The tonicity adjustment agent may be a sugar, for example dextrose, or a polyhdryic alcohol, for example mannitol. A solution may be hypertonic, substantially isotonic or hypotonic. A sufficient amount of a tonicity adjustment agent such as dextrose or mannitol may therefore be present to achieve a desired osmolality. Preferably a solution contains 50 mg/ml dextrose or mannitol.

The osmolality of a solution containing chitosan and HPMC or a poloxamer may be from 0.1 to 0.8 osmol/kg such as from 0.2 to 0.6 osmol/kg or preferably from 0.32 to 0.4 osmol/kg.

The solutions may also contain other ingredients such as an antioxidant, chelating agent or other agent generally used in pharmaceutical liquid preparations. The solution can be a sterile solution.

The solution containing chitosan and HPMC is prepared by dissolving buprenorphine or a physiologically acceptable salt or ester thereof, a chitosan and HPMC in water, typically Water for Injections. The amount of the buprenorphine or salt or ester thereof is selected so that from 0.1 to 10 mg/ml of buprenorphine or the buprenorphine salt or ester is dissolved in the solution. The required concentrations of the chitosan and of HPMC are provided too. A preservative can be dissolved in the solution. The pH of the solution can be adjusted to a value within the range from 3 to 4.8 as required. Preferably the pH is adjusted by means of hydrochloric acid.

A solution containing chitosan and a polyoxyethylene-polyoxypropylene copolymer is prepared by dissolving buprenorphine or a physiologically acceptable salt or ester thereof, a chitosan and the polyoxyethylene-polyoxypropylene copolymer in water, typically Water for Injections. The amount of the buprenorphine or salt or ester thereof is selected so that from 0.1 to 10 mg/ml of buprenorphine or the buprenorphine salt or ester is dissolved in the solution. The required concentrations of the chitosan and of the polyoxyethylene-polyoxypropylene copolymer are provided too. A preservative can be dissolved in the solution. The pH of the solution can be adjusted to a value within the range from 3 to 4.8 as required. Preferably, the pH is adjusted by means of hydrochloric acid.

Other components can be provided in the solutions at any convenient stage. For example, dextrose or mannitol may be dissolved in the water in which the buprenorphine or buprenorphine salt or ester is being dissolved. A sterile solution can be obtained either by using sterile starting materials and operating under sterile conditions and/or by using standard sterilising techniques such as passing the final solution through a sterilising filter. A pyrogen-free solution can thus be provided. The solution can then be introduced into a nasal delivery device, typically a sterile such device. If required, prior to sealing the device, the solution may be added with an inert gas such as nitrogen to protect it from oxidation.

Each of the three solutions of the invention is administered intranasally to a patient in order to induce analgesia. Rapid onset of analgesia and prolonged analgesia can thus be obtained. An effective amount of buprenorphine or a salt or ester thereof is delivered to a patient. A unit dose can be delivered to one nostril. Alternatively, half of a dose or two doses can be delivered to each nostril each administration time. The dose will depend upon a number of factors including the age and sex of the patient, the nature and extent of the pain to be treated and the period of treatment. A suitable dose of buprenorphine or a buprenorphine salt or ester is from 0.02 to 1.2 mg, such as from 50 to 600 µg or from 100 to 400 µg, calculated as buprenorphine.

Multiple doses of a solution according to the invention may be employed. For example, the rapid onset analgesia produced by the solution of the invention may permit self-titration of analgesic by the patient. The analgesic effect of an initial dose can be quickly and reliably gauged by the patient and, if insufficient, can be immediately supplemented by further dose(s) (often alternating between each nostril) until the required level of analgesia is attained. Multiple dosing may also be used in order to extend pain relief. For example, from 2 to 4 doses per day may be indicated.

The solutions of the invention may be used to treat an existing pain condition or to prevent a pain condition from occurring. An existing pain may be alleviated. Solutions of the invention can be used to treat or manage chronic or acute pain, for example the management of post-operative pain (e.g. abdominal surgery, back surgery, cesarean section, hip replacement or knee replacement).

Other medical uses include: pre-operative intranasal administration of the solution of the invention; therapy or prophylaxis adjunctive to anesthesia; post-operative analgesia; the management of trauma pain; the management of cancer pain; the management of endometriosis; the management of inflammatory pain; the management of arthritis pain (including pain associated with rheumatoid arthritis and osteoarthritis); the management of back pain; the management of myocardial pain (for example ischaemic or infarction pain); the management of dental pain; the management of neuropathic pain (e.g. diabetic neuropathy, post-herpetic neuralgia or trigeminal neuralgia); the management of colic (e.g. renal colic or gallstones), headache, migraine, fibromyalgia or dysmenorrhoea; the management of breakthrough pain associated with malignant and non-malignant disease; and the management of acute procedural pain (e.g. bone marrow aspiration or lumber puncture).

The solutions according to the invention may be administered to the nasal cavity in forms including drops or sprays. The preferred method of administration is using a spray device. Spray devices can be single (unit) dose or multiple dose systems, for example comprising a bottle, pump and actuator. Suitable spray devices are available from various commercial sources including Pfeiffer, Valois, Bespak and Becton-Dickinson.

As already mentioned, rapid onset of analgesia and prolonged analgesia can be achieved by means of the invention. The analgesic delivery profile that can be attained may avoid the relatively high $C_{max}$ values associated with intravenous administration and so lead to an improved therapeutic index. The peak plasma concentration of an analgesic that is attained after administration is defined as $C_{max}$. The invention can permit reduction or elimination of some or all of the side effects associated with the analgesic.

$C_{max}$ is typically from 1 to 5 ng/ml, for example from 1 to 4 ng/ml or from 1.5 to 3 ng/ml. $C_{max}$ may be from 1 to 2 ng/ml, especially for lower doses of buprenorphine. The time at which $C_{max}$ is reached ($T_{max}$) is typically 10 to 40 minutes after administration, for example 10 to 30 minutes or 15 to 25 minutes such as 15 to 20 minutes.

In preferred embodiments, the delivery agent is adapted to deliver the analgesic component such that $C_{max}=C_{opt}$. The term $C_{opt}$ is used in relation to analgesic drugs which exhibit a dose-response curve to analgesia which is displaced to the left with respect to the dose-response curve for side-effects. The term defines a therapeutic plasma concentration or range thereof which produces acceptable pain relief or pain amelioration but which does not produce side-effects or produces side effects which are less than those associated with higher plasma concentrations.

Preferably, the solutions of the invention enable the buprenorphine or salt or ester thereof to be delivered such that a $C_{ther}$ of 0.2 ng/ml or more, for example 0.4 ng/ml or more, is attained within 30 minutes (for example within 0.5 to 20 minutes, such as 2 to 15 minutes or 5 to 10 minutes) after introduction into the nasal cavity. The term $C_{ther}$ defines a therapeutic plasma concentration or range thereof. Thus, the term is used herein to define a blood plasma concentration (or range of plasma concentrations) of the buprenorphine or salt or ester thereof that produces pain relief or pain amelioration. $C_{ther}$ may be from 0.4 to 5 ng/ml, for example 0.4 to 1 ng/ml or 0.5 to 4 ng/ml or 0.8 to 2 ng/ml.

The $T_{maint}$ is typically at least 2 hours. The term $T_{maint}$ defines the duration of maintenance of $C_{ther}$ after administration of the analgesic. For example, the $T_{maint}$ can be from up to 24 hours, up to 12 hours or up to 6 hours such as from 2 to 4 hours or 2 to 3 hours. By means of the invention, therefore, a $C_{ther}$ of at 0.4 ng/ml may be attained within 2 to 15 minutes and maintained for a time period $T_{maint}$ of from 2 to 4' hours.

A further aspect of the invention relates to the pharmacokinetic profile that may be attained. By use of the solutions of the invention, not only can fast onset of analgesia be achieved but also prolonged analgesia can result. More generally, therefore, buprenorphine or a buprenorphine salt or ester can be combined with a delivery agent in an intranasal formulation such that, on introduction into the nasal cavity of a patient to be treated, the buprenorphine or salt or ester thereof is delivered to the bloodstream to produce within 30 minutes a therapeutic plasma concentration $C_{ther}$ of 0.2 ng/ml or greater which is maintained for a duration $T_{maint}$ of at least 2 hours.

The buprenorphine is therefore provided in a formulation suitable for nasal administration in combination with a delivery agent. The formulation is typically a liquid formulation, especially as an aqueous solution. Alternatively, the formulation may be in the form of a powder or microspheres. The buprenorphine salt may be an acid addition salt or a salt with a base. Suitable acid addition salts include the hydrochloride, sulphate, methane sulphonate, stearate, tartrate and lactate salts. The hydrochloride salt is preferred.

When the formulation is a liquid formulation, the concentration of buprenorphine or buprenorphine salt or ester is from 0.1 to 10 mg/ml, for example from 0.5 to 8 mg/ml. Preferred concentrations are 1 to 6 mg/ml, for example 1 to 4 mg/ml calculated as buprenorphine. Suitable formulations can contain buprenorphine or a buprenorphine salt or ester in an amount of 1 mg/ml or 4 mg/ml, calculated as buprenorphine.

The delivery agent is selected so that rapid onset and prolonged analgesia is obtained. The delivery agent acts to deliver the buprenorphine or buprenorphine salt or ester to the bloodstream. Thus, the delivery agent acts as an analgesic absorption modifier and any of a wide variety of delivery agents may be used providing that this functional requirement is met.

The delivery agent may comprise an absorption promoting agent. Such agents promote uptake of the analgesic component into the bloodstream. They may act via a variety of different mechanisms. Particularly preferred are mucosal adhesives. Such adhesives maintain an intimate association between the bulk analgesic composition and the nasal mucosa, so enhancing absorption and extending the $T_{maint}$ of the analgesic component. They can also be used to lower the analgesic $C_{max}$, which may be important in applications where the minimization or elimination of side-effects is desired.

Suitable absorption promoting agents include cationic polymers (particularly chitosans), surface active agents, fatty acids, chelating agents, mucolytic agents, cyclodextrins, diethylaminoethyl-dextran (DEAE-dextran; a polycationic derivative of dextran) or combinations thereof. Particularly preferred are pectins as described above having a degree of esterification of less than 50%, especially from 10 to 35%, and chitosans also as described above.

Other cationic polymers besides chitosans suitable for use as absorption promoting agents include polycationic carbohydrates. The polycationic substances preferably have a molecular weight of at least 10,000. They may be in liquid formulations at concentrations of 0.01 to 50% w/v, preferably 0.1 to 50% w/v and more preferably 0.2 to 30% w/v.

Examples of suitable polycationic polymers are polyaminoacids (e.g. polylysine), polyquaternary compounds, protamine, polyamine, DEAE-imine, polyvinylpyridine, polythiodiethyl-aminomethylethylene, polyhistidine, DEAE-methacrylate, DEAE-acrylamide, poly-p-aminostyrene, polyoxethane, co-polymethacrylates (e.g. copolymers of HPMA, N-(2-hydroxypropyl)-methacrylamide), GAFQUAT (see for example U.S. Pat. No. 3,910,862) and polyamidoamines.

Suitable surface active agents for use according to the present invention are bile salts (for example sodium deoxycholate and cholylsarcosine, a synthetic N-acyl conjugate of cholic acid with sarcosine [N-methylglycine]). Also suitable for use in the invention are bile salt derivatives (for example sodium tauro dihydrofusidate). Any of a wide range of non-ionic surfactants (e.g. polyoxyethylene-9 lauryl ether), phospholipids and lysophosphatidyl compounds (e.g. lysolecithin, lysophosphatidyl-ethanolamine, lysophosphatidylcholine, lysophosphatidylglycerol, lysophosphatidylserine and lysophosphatidic acid) may also be used. Water-soluble phospholipids may also be employed (e.g. short chain phosphatidylglycerol and phosphatidylcholines). The concentration of surface active agents used according to the invention varies according to the physicochemical properties of the surface active agent selected, but typical concentrations are in the range 0.02 to 10% w/v.

Particularly preferred surface active agents for use as absorption promoting materials are phospholipids and lysophosphatides (hydrolysis products of phospholipids), both of which form micellar structures.

When microspheres are used as the delivery agent, they are preferably prepared from a biocompatible material that will gel in contact with the mucosal surface. Substantially uniform solid microspheres are preferred. Starch microspheres (crosslinked if necessary) are preferred.

Microspheres may also be prepared from starch derivatives, modified starches (such as amylodextrin), gelatin, albumin, collagen, dextran and dextran derivatives, polyvinyl alcohol, polylactide-co-glycolide, hyaluronic acid and derivatives thereof (such as benzyl and ethyl esters), gellan gum and derivatives thereof (such as benzyl and ethyl esters) and pectin and derivatives thereof (such as benzyl and ethyl esters). The term "derivative" covers inter alia esters and ethers of the parent compound, which can be functionalised (for example to incorporate ionic groups).

Any of a wide variety of commercially available starch derivatives may be used, including hydroxyethyl starch, hydroxypropyl starch, carboxymethyl starch, cationic starch, acetylated starch, phosphorylated starch, succinate derivatives of starch and grafted starches.

Suitable dextran derivatives include, diethylaminoethyl-dextran (DEAE-dextran), dextran sulphate, dextran methyl-benzylamide sulphonates, dextran methyl-benzylamide carboxylates, carboxymethyl dextran, diphosphonate dextran, dextran hydrazide, palmitoyldextran and dextran phosphate.

The preparation of microspheres for use according to the invention may be carried out by known processes, including emulsion and phase separation methods (see for example Davis et al., (Eds), "Microspheres and Drug Therapy", Elsevier Biomedical Press, 1984, which parts relating to microsphere preparation are incorporated herein by reference). For example, albumin microspheres may be made using the water-in-oil emulsification method where a dispersion of albumin in oil is produced by homogenization or stirring, with the addition if necessary of small amounts of an appropriate surface active agent.

The size of the microspheres is largely determined by the speed of stirring or the homogenization conditions. Agitation can be provided by a simple laboratory stirrer or by more sophisticated devices (such as microfluidizers or homogenisers). Emulsification techniques may also be used to produce starch microspheres (as described in GB 1518121 and EP 223303) and for the preparation of gelatin micro spheres.

Proteinaceous microspheres may be prepared by coacervation methods. Such methods include simple or complex coacervation as well as phase separation techniques (using solvents or electrolyte solutions). Such methods are well known to those skilled in the art and details may be found in standard textbooks (for example Florence and Attwood, Physicochemical Principles of Pharmacy 2nd Ed., MacMillan Press, 1988, Chapter 8).

The microspheres may advantageously have controlled-release properties, which may be conferred by modifications of the microspheres (for example by controlling the degree of cross-linking or by the incorporation of excipients that alter the diffusional properties of the analgesic component). Alternatively, controlled release properties may be incorporated by exploiting ion-exchange chemistry (for example DEAE-dextran and chitosan are positively charged and can be used for an ion-exchange interaction with metabolites that are negatively charged).

The maximum amount of analgesic component that can be carried by the microspheres is termed the loading capacity. It is determined by the physico-chemical properties of the analgesic component and in particular its size and affinity for the matrix of the microspheres. High loading capacities can be achieved when the analgesic is incorporated into the microspheres during microsphere manufacture.

Microcapsules (which may be bioadhesive and which may also exhibit controlled release properties) may also be employed as an absorption promoting agent in the compositions of the invention. These microcapsules can be produced by a variety of methods. The surface of the capsule may be inherently adhesive or can be modified by standard coating methods known to those skilled in the art. Suitable coating materials include bioadhesive polymers such as polycarbophil, carbopol, DEAE-dextran, alginate, microcrystalline cellulose, dextran, polycarbophils and chitosan).

Oil-in-water formulations can provide for the effective nasal delivery of analgesics that are poorly soluble in water. In such applications nasal irritation may also be reduced.

The oil phase of the emulsions of the invention may comprise a hydroxylated oil, particularly a hydroxylated vegetable oil. As used herein the term "hydroxylated oil" is intended to cover any oil that contains hydroxylated fatty acids. Preferred hydroxylated oils are hydroxylated vegetable oils, and a preferred hydroxylated vegetable oil for use in the present composition is castor oil.

As used herein, the term "castor oil" is intended to include ricinus oil, oil of Palma Christie, tangantargon oil and Neoloid (as described in Merck Index, 12th Edition, p. 311), as well as the oil from *Ricinus Zanzibarinus*. The latter has a high content of glycerides of ricinoleic acid. Thus, castor oil comprises glycerides of ricinoleic acid (a hydroxy fatty acid).

When castor oil is used in the present invention, it may conveniently be obtained by cold pressing of the seeds of *Ricinus Communis* L. (family: Euphorbiaceae).

The oil phase in the emulsions of the invention may constitute 1 to 50% v/v of the emulsion. A preferred concentration of oil in the emulsion is from 10 to 40% v/v. Particularly preferred are concentrations of 20 to 30% v/v.

The emulsion compositions of the invention can be prepared using conventional methods such as by homogenisation of a mixture of the oil and analgesic component with an aqueous phase (optionally together with a stabilizing agent). Any suitable device may be used, including a microfluidizer or ultrasonic device, though microfluidizers are preferred for large scale production.

Suitable stabilizers for use in the emulsions of the invention include block copolymers containing a polyoxyethylene block (i.e. a block made up of repeating ethylene oxide moieties). An example of a suitable stabilizer of this type is Poloxamer™. Other suitable stabilizers include phospholipid emulsifiers (for example soy and egg lecithins). Particularly preferred is the egg lecithin Lipoid E80™ (from Lipoid™), which contains both phosphatidylcholine and phosphatidyl ethanoline. Other suitable phospholipids include phospholipid-polyethylene glycol (PEG) conjugates (see for example Litzinger et al., Biochem Biophys Acta, 1190 (1994) 99-107).

Any suitable concentration of stabilizer/emulsifier may be used, and it typically falls within the range 0.1 to 10% w/v in the aqueous phase of the emulsion. Particularly preferred are concentrations of 1 to 5% w/v.

The stability of the emulsion can be enhanced by the addition of one or more co-emulsifier(s). Suitable pharmaceutically-acceptable co-emulsifiers include fatty acids, bile acids and salts thereof. Preferred fatty acids have greater than 8 carbon atoms, and particularly preferred is oleic acid. Of the suitable bile acids, preferred is deoxycholic acid. Suitable salts pf the foregoing include the alkali metal (e.g. Na and K) salts. Co-emulsifiers can be added at a concentration of 1% w/v or less on the aqueous phase.

Buffering agents may also be used in the composition. For example, a buffer may used to maintain a pH that is compatible with nasal fluid, to preserve emulsion stability and/or to ensure that the analgesic component does not partition from the emulsion oil phase into the aqueous phase.

It will be clear to the person skilled in the art that additional components can also be added to the emulsion including thickening and gelling agents (such as cellulose polymers, particularly sodium carboxymethyl cellulose, alginates, gellans, pectins, acrylic polymers, agar-agar, gum tragacanth, gum xanthan, hydroxyethyl cellulose, chitosan, as well as block copolymers of polyoxyethylene-polyoxypropylene). Preservative agents such as methyl parabenzoates, benzylalcohol and chlorobutanol may also be added.

The delivery agent may comprise a liposome. Liposomes are microscopic vesicles composed of an aqueous compartment surrounded by a phospholipid bilayer that acts as a permeable entrapment barrier. Many different classes of liposomes are known (see Gregoriadis (ed.) in Liposome Technology, 2nd edition, vol I-III, CRC Press, Boca Ranto, Fla., 1993). Some liposomes can provide controlled sustained release of the encapsulated drug. In such systems, the rate of drug release is determined by the liposome's physicochemical properties. Liposomes can be tailored for a specific application by modification of size, composition, and surface charge to provide the desired rate of drug delivery (see Meisner D, et al: In Proceedings, 15th International Symposium on Controlled Release of Bioactive Materials. 15:262-263, 1988; Mezei M: In Drug Permeation Enhancement, Theory and Application. Hsieh DS (ed.): Marcel Dekker Inc., New York, 1993, pp 171-198; and Meisner D, et al: J Microencapsulation 6:379-387, 1989). Thus, liposome-encapsulation can act as an effective and safe delivery agent in the compositions of the invention.

The sustained release property of the liposomal product can be regulated by the nature of the lipid membrane and by the inclusion of other excipients in the composition of the liposomal products. Current liposome technology permits a reasonable prediction on the rate of drug release based on the composition of the liposome formulation. The rate of drug release is primarily dependent on the nature of the phospholipids, e.g. hydrogenated (—H) or unhydrogenated (—G), or the phospholipid/cholesterol ratio (the higher this ratio, the faster the rate of release), the hydrophilic/lipophilic properties of the active ingredients and by the method of liposome manufacturing.

Materials and procedures for forming liposomes are well known to those skilled in the art and include ethanol or ether injection methods. Typically, the lipid is dissolved in a solvent and the solvent evaporated (often under reduced pressure) to produce a thin film. The film is then hydrated with agitation. The analgesic component is incorporated at the lipid film forming stage (if lipophilic) or at the hydration phase as part of the aqueous hydrating phase (if hydrophilic). Depending on the hydration conditions selected and the physicochemical properties of the lipid(s) used, the liposomes can be multilamellar lipid vesicles (MLV), unilamellar lipid vesicles (including small unilamellar vesicles (SUV) and large unilamellar vesicles (LUV)) and as multivesicular liposomes.

Lipid components typically comprise phospholipids and cholesterol while excipients may comprise tocopherol, antioxidants, viscosity inducing agents and/or preservatives. Phospholipids are particularly useful, such as those selected from the group consisting of phosphatidylcholines, lysophosphatidylcholines, phosphatidylserines, phosphatidylethanolamines, and phosphatidylinositols. Such phospholipids may be modified using, for example, cholesterols, stearylamines, stearic acid, and tocopherols.

The compositions of the invention may further comprise other suitable excipients, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

Excipients such as humectants, isotoning agents, antioxidants, buffers and/or preservatives are preferably used. Formulation and dosage would depend on whether the analgesic is to be used in the form of drops or as a spray (aerosol). Alternatively, suspensions, ointments and gels can be applied to the nasal cavity. However, it is known that nasal mucous membranes are also capable of tolerating slightly hypertonic solutions. Should a suspension or gel be desired instead of a solution, appropriate oily or gel vehicles may be used or one or more polymeric materials may be included, which desirably should be capable of conferring bioadhesive characteristics to the vehicle.

Many other suitable pharmaceutically acceptable nasal carriers will be apparent to those skilled in the art. The choice of suitable carriers will depend on the exact nature of the particular nasal dosage form desired, for example whether the drug is to be formulated into a nasal solution (for use as drops or as a spray), a nasal suspension, a nasal ointment or a nasal gel. In another embodiment, nasal dosage forms are solutions, suspensions and gels, which contain a major amount of water (preferably purified water) in addition to the active ingredient. Minor amounts of other ingredients such as pH adjusters (e.g. a base such as NaOH), emulsifiers or dispersing agents, buffering agents, preservatives, wetting agents and jelling agents (e.g., methylcellulose) may also be present.

The nasal compositions of the invention may be isotonic, hypertonic or hypotonic. If desired, sustained release nasal compositions, e.g. sustained release gels, can be readily prepared, preferably by employing the desired drug in one of its relatively insoluble forms, such as the free base or an insoluble salt.

The composition of the present invention may be adjusted, if necessary, to approximately the same osmotic pressure as that of the body fluids (i.e. isotonic). Hypertonic solutions can irritate the delicate nasal membranes, while isotonic compositions do not. Isotonicity can be achieved by adding glycerol or an ionic compound to the composition (for example, sodium chloride). The compositions may take the form of a kit of parts, which kit may comprise the intranasal composition together with instructions for use and/or unit dosage containers and/or an intranasal delivery device.

The compositions of the invention enable the buprenorphine or salt or ester thereof to be delivered such that a $C_{ther}$ of 0.2 ng/ml or more, for example 0.4 ng/ml or more, is attained within 30 minutes (for example within 0.5 to 20 minutes, such as 2 to 15 minutes or 5 to 10 minutes) after introduction into the nasal cavity. The term $C_{ther}$ defines a therapeutic plasma concentration or range thereof. Thus, the term is used herein to define a blood plasma concentration (or range of plasma concentrations) of the buprenorphine or salt or ester thereof that produces pain relief or pain amelioration. $C_{ther}$ may be from 0.4 to 5 ng/ml, for example 0.4 to 1 ng/ml or 0.5 to 4 ng/ml or 0.8 to 2 ng/ml.

The $T_{maint}$ is typically at least 2 hours. The term $T_{maint}$ defines the duration of maintenance of $C_{ther}$ after administration of the analgesic. For example, the $T_{maint}$ can be from up to 24 hours, up to 12 hours or up to 6 hours such as from 2 to 4 hours or 2 to 3 hours. By means of the invention, therefore, a $C_{ther}$ of at 0.4 ng/ml may be attained within 2 to 15 minutes and maintained for a time period $T_{maint}$ of from 2 to 4 hours.

As already mentioned, rapid onset of analgesia and prolonged analgesia can be achieved. The analgesic delivery profile that can be attained may avoid the relatively high $C_{max}$ values associated with intravenous administration and so lead to an improved therapeutic index. The peak plasma concentration of an analgesic that is attained after administration is defined as $C_{max}$. The invention can permit reduction or elimination of some or all of the side effects associated with the analgesic.

$C_{max}$ is typically from 1 to 5 ng/ml, for example from 1 to 4 ng/ml from 1.5 to 3 ng/ml. $C_{max}$ may be from 1 to 2 ng/ml, especially for lower doses of buprenorphine. The time at which $C_{max}$ is reached ($T_{max}$) is typically 10 to 40 minutes after administration, for example 10 to 30 minutes or 15 to 25 minutes such as 15 to 20 minutes.

In preferred embodiments, the delivery agent is adapted to deliver the analgesic component such that $C_{max}=C_{opt}$. The term $C_{opt}$ is used in relation to analgesic drugs which exhibit a dose-response curve to analgesia which is displaced to the left with respect to the dose-response curve for side-effects. The term defines a therapeutic plasma concentration or range thereof which produces acceptable pain relief or pain amelioration but which does not produce side-effects or produces side effects which are less than those associated with higher plasma concentrations.

The compositions of the invention are administered intranasally to a patient in order to induce analgesia. An effective amount of buprenorphine or a salt or ester thereof is delivered to a patient. As previously mentioned, a unit dose can be delivered to one nostril. Alternatively, half of a dose or two doses can be delivered to each nostril each administration time. The dose will depend upon a number of factors including the age and sex of the patient, the nature and extent of the pain to be treated and the period of treatment. A suitable dose of buprenorphine or a buprenorphine salt or ester is from 0.02 to 1.2 mg, such as from 50 to 600 µg or from 100 to 400 µg, calculated as buprenorphine.

Multiple doses of a composition according to the invention may be employed. For example, the rapid onset analgesia produced by the solution of the invention may permit self-titration of analgesic by the patient. The analgesic effect of an initial dose can be quickly and reliably gauged by the patient and, if insufficient, can be immediately supplemented by further dose(s) (often alternating between each nostril) until the required level of analgesia is attained. Multiple dosing may also be used in order to extend pain relief. For example, from 2 to 4 doses per day may be indicated.

The compositions of the invention may be used to treat an existing pain condition or to prevent a pain condition from occurring. An existing pain may be alleviated. Compositions can be used to treat or manage chronic or acute pain, for example the management of post-operative pain (e.g. abdominal surgery, back surgery, cesarean section, hip replacement or knee replacement). Other medical uses have been described above.

When in the form of a solution, compositions according to the invention may be administered to the nasal cavity in forms including drops or sprays. The preferred method of administration is using a spray device. Spray devices can be single (unit) dose or multiple dose systems, for example comprising a bottle, pump and actuator. Suitable spray devices are available from various commercial sources including Pfeiffer, Valois, Bespak and Becton-Dickinson.

When in the form of powder or microspheres, a nasal insufflator device may be employed. Such devices are already in use for commercial powder systems intended for nasal application. The insufflator may be used to produce a fine, dispersed plume of the dry powder or microspheres. The insufflator is preferably provided with means for administering a predetermined dose of the analgesic composition. Powder or microspheres may be contained in a bottle or container adapted to be used with the insufflator. Alternatively, powders or microspheres may be provided in capsules (e.g. gelatin capsules) or other single dose devices adapted for nasal administration, in which embodiments the insufflator may comprise means for breaking open the capsule (or other single dose device).

The following Examples illustrate the invention.

EXAMPLE 1

Nasal Solution Containing Buprenorphine (4 mg/ml) and Pectin 5 g of pectin (SLENDID (trade mark) 100, CP Kelco, Denmark) was dissolved by stirring into approximately 180 ml of water for injection (WFI) (Baxter, UK). 1075 mg of buprenorphine hydrochloride (MacFarlan Smith, UK) and 12.5 g of dextrose (Roquette) were dissolved into the pectin solution. 1.25 ml of phenylethyl alcohol (R. C. Treat, UK) and 50 mg of propyl hydroxybenzoate (Nipa, UK) were dissolved into the pectin/buprenorphine solution. The solution was adjusted to 250 ml using WFI. 1M hydrochloric acid (BDH, UK) was added to adjust the pH to 3.6.

The final product was a slightly turbid solution 4.3 mg/ml buprenorphine hydrochloride (corresponding to 4 mg/ml buprenorphine), 20 mg/ml pectin, 50 mg/ml dextrose, 5 µl/ml phenylethyl alcohol and 0.2 mg/ml propyl hydroxybenzoate. The pH of the solution was 3.6, as mentioned above. The osmolality of the solution was 0.46 osmol/kg.

Single dose nasal spray devices (Pfeiffer, Germany) were filled with the solution. Each device was filled with 123 µl of liquid. Actuation of the device delivered a dose of 100 µl of liquid containing 400 µg of buprenorphine and 2 mg of pectin.

EXAMPLE 2

Nasal Solution Containing Buprenorphine (2 mg/ml) and Pectin 5 g of pectin is dissolved by stirring into approximately 180 ml of WFI. 538 mg of buprenorphine hydrochloride and 12.5 g of dextrose are dissolved into the pectin solution. 1.25 ml of phenylethyl alcohol and 50 mg of propyl hydroxybenzoate are dissolved into the pectin/buprenorphine solution. The solution is adjusted to 250 ml using WFI.

The final product is a slightly turbid solution containing 2.16 mg/ml buprenorphine hydrochloride (corresponding to 2 mg/ml buprenorphine), 20 mg/ml pectin, 50 mg/ml dextrose, 5 µl/ml phenylethyl alcohol and 0.2 mg/ml propyl hydroxybenzoate.

123 µl of the above solution is filled into a Valois Monospray single dose nasal spray device (Pfeiffer, Germany). Actuation of the device will deliver a dose of 100 µl of liquid containing 200 µg of buprenorphine and 2 mg of pectin.

EXAMPLE 3

Nasal Solution Containing Buprenorphine (4 mg/ml), Chitosan and HPMC 0.75 g of HPMC (Methocel (trade mark) E4M, Colorcon, UK) was dispersed into approximately 125 ml of pre-heated (70-80° C.) water for injection (WFI) (Baxter, UK). The HPMC dispersion was stirred in an ice bath until a clear solution had formed. 1.25 g of chitosan glutamate (Protosan (trade mark) UPG213, Pronova, Norway) was dissolved in the HPMC solution. 75 mg of 50% w/w benzalkonium chloride solution (Albright and Wilson, UK) was dispersed in 10 ml of WFI and transferred with an additional 40 ml of WFI to a 250 ml volumetric flask. 1075 mg of buprenorphine hydrochloride (MacFarlan Smith, UK) and 12.5 g of dextrose (Roquette, UK) were transferred into the volumetric flask. The chitosan/HPMC solution and an additional 40 ml of WFI were added to the flask. The solution was adjusted to pH 3.4 using 1M hydrochloric acid solution (BDH, UK) and the flask contents adjusted to 250 ml using WFI.

The final product was a clear colourless solution containing a 4.3 mg/ml buprenophine hydrochloride (corresponding to 4 mg/ml buprenorphine), 5 mg/ml chitosan glutamate, 3 mg/ml HPMC, 50 mg/ml dextrose and 0.15 mg/ml benzalkonitum chloride. The osmolality of the final solution was 0.34 osmol/kg and the viscosity, as measured using a Brookfield CP70 cone and plate viscometer was 84.7 cps at 2.5 rpm and 25° C.

Single dose nasal spray devices (Pfeiffer, Germany) were filled with the solution. Each device was filled with 123 µl of liquid. Actuation of the device delivered a dose of 100 µl of liquid containing 400 µg of buprenorphine, 0.5 mg of chitosan and 0.3 mg of HPMC. Hence, a dose of 400 µg buprenorphine is provided by a single spray into one nostril. A dose of 800 µg is provided by a single spray into each nostril.

EXAMPLE 4

Nasal Solution Containing Buprenorphine (1 mg/ml), Chitosan and HPMC

A solution containing HPMC, chitosan glutamate and benzalkonium chloride is prepared according to Example 3. 269 mg of buprenorphine hydrochloride and 12.5 g of mannitol (Sigma, UK) are transferred into the volumetric flask. The chitosan/HPMC solution and an additional 40 ml of WFI are added to the flask. The pH of the solution is adjusted to pH 3.6 using 1 M hydrochloric acid solution and the flask contents adjusted to 250 ml using WFI.

The final product is a clear colourless solution containing 1.08 mg/ml buprenorphine hydrochloride (corresponding to 1 mg/ml buprenorphine), 5 mg/ml chitosan glutamate, 3 mg/ml HPMC, 50 mg/ml mannitol and 0.15 mg/ml benzalkonium chloride.

123 µl of the above solution is filled into a single dose nasal spray device (Pfeiffer, Germany). Actuation of the device will deliver a dose of 100 1l of liquid containing 100 µg of buprenorphine, 0.5 mg of chitosan and 0.3 mg of HPMC.

5 ml of the solution is filled into a 10 ml glass bottle. A Valois VP7, 100 µl pump and actuator (Valois, France) are attached to the bottle. When primed, the pump will dispense 100 µl of solution containing 100 µg of buprenorphine.

EXAMPLE 5

Nasal Solution Containing Buprenorphine (4 mg/ml), Chitosan and Poloxamer 25 g of poloxamer 188 (Lutrol (trade mark) F-68, BASF, Germany) was dissolved by stirring into 100 ml of water for injection (WFI) (Baxter, UK) at a temperature of 2 to 8° C. 1.25 g of chitosan glutamate (Protasan (trade mark) UPG213, Pronova, Norway) was dissolved in the poloxamer solution. 75 mg of 50% w/w benzalkonium chloride solution (Albright and Wilson, UK) was dispersed in 10 ml of WFI and transferred with an additional 40 ml of WFI to a 250 ml volumetric flask. 1075 mg of buprenorphine hydrochloride (MacFarlan Smith, UK) and 12.5 g of dextrose (Roquette, UK) were transferred into the volumetric flask. The chitosan/poloxamer solution and an additional 40 ml of WFI were added to the flask. The solution was adjusted to pH 3.4 using 1M hydrochloric acid solution (BDH, UK) and the flask contents adjusted to 250 ml using WFI.

The final product was a clear colourless solution containing 4.3 mg/ml buprenorphine hydrochloride (corresponding to 4 mg/ml buprenorphine), 5 mg/ml chitosan glutamate, 100 mg/ml poloxamer 188, 50 mg/ml dextrose and 0.15 mg/ml benzalkonium chloride. The osmolality of the final solution was 0.60 Osmol/kg.

Single dose nasal spray devices (Pfeiffer, Germany) were filled with the solution. Each device was filled with 123 µl of liquid. Actuation of the device delivered a dose of 1001 µl of liquid containing 400 µg of buprenorphine, 0.5 mg of chitosan and 10 mg of poloxamer 188.

EXAMPLE 6

Nasal Solution Containing Buprenorphine (1 mg/ml), Chitosan and Poloxamer

A solution containing chitosan glutamate, poloxamer 188 and benzalkonium chloride is prepared according to Example 5. 269 mg of buprenorphine hydrochloride and 12.5 g mannitol (Sigma, UK) are transferred into the volumetric flask. The chitosan/poloxamer solution and an additional 40 ml of WFI are added to the flask. The pH of the solution is adjusted to pH 3.6 using 1 M hydrochloric acid and the flask contents adjusted to 250 ml using WFI.

The final product is a clear colourless solution containing 1.08 mg/ml buprenorphine hydrochloride (corresponding to 1 mg/ml buprenorphine), 5 mg/ml chitosan glutamate, 100 mg/ml poloxamer 188, 50 mg/ml mannitol and 0.15 mg/ml benzalkonium chloride.

123 µl of the above solution is filled into a single dose nasal spray device (Pfeiffer, Germany). Actuation of the device will deliver a dose of 100 µl of liquid containing 100 µg of buprenorphine, 0.5 mg of chitosan and 10 mg of poloxamer 188.

4 ml of the solution is filled into a 5 ml glass bottle. A Pfeiffer 100 µl nasal spray pump and actuator are attached to the bottle. When primed, the pump will dispense 100 µl of solution containing 100 µg of buprenorphine.

EXAMPLE 7

Effects of Varying Parameters of Buprenorphine-pectin Solutions

General Methods

The appearance, pH (Mettler MP230 pH meter) and osmolality (Osmomat 030 cryoscopic osmometer) of the solutions were determined.

The viscosity of the solution was measured using a Brookfield Cone and Plate Rheometer. Results given are the mean of determinations at three rotation speeds appropriate to the viscosity of the solution.

The spray characteristics from a Pfeiffer multi-dose nasal spray device (standard nozzle, 0.1 ml pump, Cat. No. 62897) were evaluated by measurement of plume angle using image analysis. Results given are the mean of four determinations (two at one orientation and two at a 90 rotation to the first orientation) The buprenorphine content of formulations was determined by hplc.

Gels were prepared by controlled mixing of 20 ml of formulation with 5 ml of a standard calcium chloride solution (9.44 mg/ml $CaCl_2.2H_2O$) before standing for 1 hour at room temperature. A visual assessment of the structure, uniformity, clarity and evidence of syneresis of each gel was conducted and, in addition, the gel structure was examined with a Stable Microsystems Texture Analyser. Results (from single determinations) are expressed in terms of force (maximum penetration force) and area (total work of gel penetration).

Effect of Pectin Concentration on Appearance Solution/Gel Properties and Spray Characteristics 1. Methods Buprenorphine hydrochloride (107.5 mg) and anhydrous dextrose (1.25 g) were stirred in 18-20 ml water in a 25 ml volumetric flask together with an appropriate quantity of pectin and the mixture stirred overnight or until a solution formed. The mixture was then made up to 25 ml with water to give a solution containing 4 mg/ml buprenorphine, 50 mg/ml dextrose and 1, 5, 10, 20, 30, 40 or 80 mg/ml pectin and the pH, appearance, osmolality, viscosity were determined. In addition, spray characteristics from a Pfeiffer multi-dose nasal spray device (standard nozzle, 0.1 ml pump, Cat. No. 62897) were evaluated by measurement of plume angle using image analysis. Gels were prepared by controlled mixing of 20 ml of formulation with 5 ml of a standard calcium chloride solution (9.44 mg/ml $CaCl_2.2H_2O$) before standing for 1 hour at room temperature. A visual assessment of the structure, uniformity, clarity and evidence of syneresis of each gel was conducted and, in addition, the gel structure was examined with a Stable Microsystems Texture Analyser.

An in vitro method was employed to simulate the gelling that may occur when the pectin formulation comes into contact with the nasal mucosal surface. This involved adding 2 ml of each formulation to an equal volume of simulated nasal electrolyte solution (SNES) (comprised 8.77 g/l sodium chloride, 2.98 g/l potassium chloride and 0.59 g/l calcium chloride dihydrate) and agitating gently. The mixtures were left to stand for 1 hour at room temperature before visual assessment.

2. Results

As pectin concentration increased, solutions became increasingly turbid, osmolality and viscosity increased and plume angle decreased (Table 1). An excellent relationship was obtained between concentration and plume angle up to 30 mg/ml pectin. The pH was not significantly affected by pectin concentration.

Upon addition of calcium ions pectin formed visually satisfactory gels in the concentration range 5-20 mg/ml (Table 2). Correspondingly greater integrity of gel structure was noted over this range. At higher pectin concentrations texture analysis results were inconclusive because homogeneity of the gel is difficult to control and increasing syneresis was observed.

At a lower calcium ion concentration (SNES) pectin produced mobile gels at 10-20 mg/ml and strong, inhomogeneous gels at higher concentrations.

TABLE 1

Appearance, pH, osmolality, viscosity and spray characteristics (plume angle) of buprenorphine solutions containing 4.3 mg/ml buprenorphine hydrochloride (BPN•HCl), 50 mg/ml dextrose and different concentrations of pectin (Slendid 100).

| Batch No. | Pectin Conc. (mg/ml) | pH | Osmolality (osmol/kg) | Viscosity (cps) | Plume angle (°) | Appearance |
|---|---|---|---|---|---|---|
| 105 | 1 | 4.4 | 0.32 | 1.4 | 56 | Clear, colourless solution |
| 106 | 5 | 4.2 | 0.33 | 2.1 | 53 | Very slightly turbid, colourless solution |
| 107 | 10 | 4.1 | 0.34 | 3.7 | 42 | Slightly turbid, colourless solution |
| 108 | 20 | 4.0 | 0.37 | 9.0 | 29 | Slightly turbid, pale yellow solution |
| 153 | 30 | 3.9 | 0.40 | 16.8 | 21 | Turbid, pale yellow solution |
| 109 | 40 | 4.0 | 0.43 | 33.9 | 20 | Turbid, pale yellow solution |
| 110 | 80 | 4.0 | 0.55 | N/M* | 16 | Very turbid, pale yellow solution |

*N/M = not measurable

TABLE 2

Gelling properties of buprenorphine solutions containing 4.3 mg/ml BPN•HCl, 50 mg/ml dextrose and different concentrations of pectin (Slendid 100) when mixed with a standard calcium chloride solution.

| Batch No. | Pectin Conc. (mg/ml) | Texture analysis Force (g) | Texture analysis Area (g s) | Visual assessment |
|---|---|---|---|---|
| 105 | 1 | — | — | Clear, slightly viscous, colourless solution. Did not gel. |
| 106 | 5 | 116 | 1420 | Slightly opalescent, strong, uniform gel with minimum syneresis. |
| 107 | 10 | 220 | 3858 | Semi-transparent, strong, uniform gel with minimum syneresis. |
| 108 | 20 | 279 | 4872 | Semi-transparent, pale yellow, strong, uniform gel with minimum syneresis. |
| 153 | 30 | 190 | 4259 | Semi-transparent, pale yellow, strong, uniform gel with some syneresis. |
| 109 | 40 | 234 | 2691 | Semi-transparent, pale yellow, very strong, non-uniform gel with some syneresis. |
| 110 | 80 | 303 | 5356 | Semi-transparent, yellow, extremely strong, non-uniform gel with significant syneresis. |

TABLE 2a

Gelling properties of buprenorphine solutions containing 4.3 mg/ml BPN•HCl, 50 mg/ml dextrose and different concentrations of pectin (Slendid 100) when mixed with SNES.

| Batch No. | Pectin Conc. (mg/ml) | Visual assessment |
|---|---|---|
| 161 | 1 | Clear, slightly viscous, colourless solution. Did not gel. |
| 162 | 5 | Clear, viscous, colourless solution. Did not gel. |
| 163 | 10 | Clear, colourless, weak diffuse gel. |
| 164 | 20 | Pale yellow, semi-transparent weak diffuse gel. |
| 165 | 30 | Semi-transparent pale yellow, strong gel with some syneresis. |
| 166 | 40 | Semi-transparent pale yellow, strong gel with some syneresis. |
| 167 | 80 | Opaque pale yellow, very strong gel with significant syneresis. |

Effect of pH on Solubility and Gelling Properties of Buprenorphine Hydrochloride 1. Methods Stock solutions containing pectin (Slendid 100) (20 mg/ml) and dextrose (50 mg/ml) were prepared at various pH in the range pH 3.0 to 6.0 (pH adjustments were made with 0.1 M HCl or 0.1 M meglumine). An excess of buprenorphine hydrochloride was then stirred overnight at 18° C. in 5 or 25 ml of each solution. Saturated solutions were recovered by passing each mixture through a 0.2 μm polycarbonate membrane filter. The concentration of buprenorphine hydrochloride in the filtrate was determined by hplc.

In preliminary experiments addition of excess buprenorphine hydrochloride was found to reduce the pH of the (un-buffered) solutions. In order to produce solution at the higher end of the desired pH range, a minimal excess of buprenorphine hydrochloride was added to solutions (5 ml) containing pectin (Slendid 100) (20 mg/ml) and dextrose (50 mg/ml) adjusted to various pH values in the range pH 4.5 to 6.0 with 0.1 M HCl or 0.1 M meglumine. The quantity of excess buprenorphine hydrochloride added was based on preliminary findings and on reported solubility data for buprenorphine hydrochloride (Cassidy et al, J. Controlled Release 25, 21-29, 1993). Following overnight stirring at 18° C., mixtures were examined to confirm that undissolved drug remained before saturated solutions were recovered by passing each mixture through a 0.2 μm polycarbonate membrane filter.

For selected formulations gels were prepared by controlled mixing of 20 ml of formulation with 5 ml of a standard calcium chloride solution (9.44 mg/ml $CaCl_2.2H_2O$) before standing for 1 hour at room temperature. A visual assessment of the structure, uniformity, clarity and evidence of syneresis of each gel was conducted and, in addition, the gel structure was examined with a Stable Microsystems Texture Analyser.

2. Results

Buprenorphine was sparingly soluble (greater than 10 ng/ml) in aqueous solutions containing 20 mg/ml pectin +50 mg/ml dextrose at pH below 4.4 (Table 3). In general, solubility fell as pH increased above 4.5 (Table 3a). Solutions were slightly soluble (less than 10 ng/ml) at pH 4.5-6.0.

Gelling properties were largely unaffected by pH (and therefore by buprenorphine concentration) (Table 4).

TABLE 3

Solubility of BPN•HCl at pH 3.2-4.0 in solutions containing 20 mg/ml pectin (Slendid 100) and 50 mg/ml dextrose.

| Batch No. | Final pH | Buprenorphine detected* (mg/ml) |
|---|---|---|
| 043 | 3.2 | 12.3 |
| 085 | 3.6 | 14.2 |
| 086 | 3.8 | 13.5 |
| 087 | 3.9 | 15.8 |
| 048 | 4.0 | 14.3 |

*Expressed as buprenorphine free base

TABLE 3a

Solubility of BPN•HCl at pH 4.4-5.3 in solutions containing 20 mg/ml pectin (Slendid 100) and 50 mg/ml dextrose.

| Batch No. | Final pH | Buprenorphine detected* (mg/ml) |
|---|---|---|
| 202 | 4.4 | 11.6 |
| 203 | 4.5 | 9.0 |
| 204 | 4.7 | 7.3 |
| 205 | 4.7 | 6.0 |
| 206 | 4.8 | 3.5 |
| 207 | 5.1 | 2.7 |
| 209 | 5.2 | 1.4 |
| 208 | 5.3 | 1.3 |

*Expressed as buprenorphine free base

TABLE 4

Effect of pH on the gelling properties of BPN•HCl in solution containing 20 mg/ml pectin (Slendid 100) and 50 mg/ml dextrose when mixed with a standard calcium chloride solution.

| Batch No. | pH (actual) | Texture analysis* Force (g) | Texture analysis* Area (g s) | Visual assessment |
|---|---|---|---|---|
| 043 | 3.0 (3.2) | 328 | 4439 | Semi-transparent, uniform gel with minimum syneresis. |
| 086 | 3.5 (3.8) | 309 | 4018 | Semi-transparent, uniform gel with minimum syneresis. |
| 048 | 4.0 (3.9) | 371 | 4056 | Semi-transparent, uniform gel with minimum syneresis. |
| 089 | 5.5 (5.1) | 168 | 1620 | Semi-transparent, uniform gel with some syneresis. |

*Reduced volumes (14 ml of formulation and 3.5 ml of $CaCl_2 \cdot 2H_2O$) were used due to higher than expected loss of volume during filtration.

Effect of Osmolality (Dextrose or Mannitol Concentration) on Viscosity Spray Characteristics and Gelling Properties of Buprenorphine Hydrochloride 1. Methods Buprenorphine hydrochloride (107.5 mg) and pectin (Slendid 100) (500 mg) were stirred in 18-20 ml water in a 25 ml volumetric flask together with an appropriate quantity of anhydrous dextrose or mannitol and the mixture stirred overnight or until a solution formed. The mixture was then made up to 25 ml with water to give a solution containing 4 mg/ml buprenorphine, 20 mg/ml pectin and 15, 50, 87, 122, 157 or 192 mg/ml dextrose (or 15, 50, 87, 122 mg/ml mannitol) and the pH, appearance, osmolality, viscosity were determined. In addition, spray characteristics from a Pfeiffer multi-dose nasal spray device (standard nozzle, 0.1 ml pump, Cat. No. 62897) were evaluated by measurement of plume angle using image analysis. Gels were prepared by controlled mixing of 20 ml of formulation with 5 ml of a standard calcium chloride solution (9.44 mg/ml $CaCl_2.2H_2O$) before standing for 1 hour at room temperature. A visual assessment of the structure, uniformity, clarity and evidence of syneresis of each gel was conducted and, in addition, the gel structure was examined with a Stable Microsystems Texture Analyser.

2. Results

As dextrose concentration increased from 15 to 50 mg/ml spray characteristics from a nasal spray device were affected as indicated by a decrease in plume angle associated with an increase in viscosity: a narrow plume was consistently obtained above 50 mg/ml dextrose (Table 5). As mannitol concentration increased there was a slight increase in viscosity and a slight decrease in plume angle (Table 6).

Gel structure may have been slightly weakened as dextrose concentration increased. This was indicated by a visual assessment but texture analysis results were inconclusive (Table 7).

Gel structure was affected at higher mannitol concentration. Visual assessment and texture analysis indicated that less uniform and weaker gels were produced (Table 8).

TABLE 5

Osmolality, viscosity and spray characteristics of 4.3 mg/ml BPN•HCl/20 mg/ml pectin (Slendid 100) solution containing varying concentrations of dextrose.

| Batch No. | Dextrose concentration (mg/ml) | Osmolality (osmol/kg) | Viscosity (cps) | Plume angle (°) |
|---|---|---|---|---|
| 114 | 15 | 0.15 | 8.0 | 43 |
| 115 | 50 | 0.37 | 9.2 | 30 |
| 116 | 87 | 0.62 | 10.3 | 22 |
| 117 | 122 | 0.88 | 11.5 | 19 |
| 118 | 157 | 1.18 | 13.0 | 23 |
| 119 | 192 | 1.5 | 14.5 | 17 |

TABLE 6

Osmolality, viscosity and spray characteristics of 4.3 mg/ml BPN•HCl/20 mg/ml pectin (Slendid 100) solution containing varying concentrations of mannitol.

| Batch No. | Mannitol conc. (mg/ml) | Osmolality (osmol/kg) | Viscosity (cps) | Plume angle (°) |
|---|---|---|---|---|
| 120 | 15 | 0.16 | 8.4 | 33 |
| 121 | 50 | 0.37 | 9.2 | 22 |
| 122 | 87 | 0.61 | 10.3 | 22 |
| 123 | 122 | 0.85 | 11.3 | 21 |
| 124 | 157* | — | — | — |
| 125 | 192* | — | — | — |

*Did not dissolve

TABLE 7

Gelling properties of 4.3 mg/ml BPN•HCl/20 mg/ml pectin (Slendid 100) solution containing varying concentrations of dextrose.

| Batch No. | Osmolality (osmol/kg) | Texture analysis Force (g) | Texture analysis Area (g s) | Visual assessment |
|---|---|---|---|---|
| 114 | 0.15 | 574 | 10338 | Very strong, uniform, semi-transparent pale yellow gel with minimum syneresis. |
| 115 | 0.37 | 359 | 6589 | Very strong; uniform, semi-transparent pale yellow gel with minimum syneresis. |
| 116 | 0.62 | 280 | 5520 | Strong, uniform, semi-transparent pale yellow gel with minimum syneresis. |
| 117 | 0.88 | 336 | 5019 | Strong, uniform, semi-transparent pale yellow gel with minimum syneresis. |
| 118 | 1.18 | 467 | 7066 | Strong, uniform, semi-transparent pale yellow gel with minimum syneresis. |
| 119 | 1.5 | 249 | 3435 | Strong; uniform, semi-transparent pale yellow gel with some syneresis. |

TABLE 8

Gelling properties of 4.3 mg/ml BPN•HCl/20 mg/ml pectin (Slendid 100) solution containing varying concentrations of mannitol when mixed with a standard calcium chloride solution.

| Batch No. | Osmolality (osmol/kg) | Texture analysis Force (g) | Texture analysis Area (g s) | Visual assessment |
|---|---|---|---|---|
| 120 | 0.16 | 477 | 9006 | Strong, uniform, semi-transparent pale yellow gel with some syneresis. |
| 121 | 0.37 | 497 | 8991 | Strong, uniform, semi-transparent pale yellow gel with some syneresis. |
| 122 | 0.61 | 358 | 7160 | Weak, non-uniform, semi-transparent pale yellow gel with some syneresis |
| 123 | 0.85 | 221 | 3881 | Weak, non-uniform, semi-transparent pale yellow gel with some syneresis |

Effect of Dextrose and Mannitol Concentration on Buprenorphine Solubility

1. Methods

Solutions containing pectin (Slendid 100) (20 mg/ml) were prepared at pH 3, 4, 5 and 6 (pH adjustments were made with 0.1M HCl or 0.1M meglumine). Into 5 ml of each solution was dissolved 0, 62.5, 125, 187.5 or 200 mg anhydrous dextrose or mannitol to give approximate dextrose/mannitol concentrations of 0, 12.5, 25, 37.5 or 50 mg/ml respectively. An excess of buprenorphine hydrochloride was then added and the mixture stirred overnight at 18° C. Saturated buprenorphine hydrochloride solutions were produced by passing each mixture through a 0.2 μm polycarbonate membrane filter. The concentration of buprenorphine hydrochloride in the filtrate was determined by hplc.

2. Results

Buprenorphine solubility in aqueous solution containing 20 mg/ml pectin was not affected significantly by dextrose (Table 9) or mannitol (Table 10) concentration across the measured pH range.

TABLE 9

Effect of dextrose concentration on the solubility of BPN•HCl in solution containing 20 mg/ml pectin (Slendid 100).

| Batch No. | Dextrose concentration (mg/ml) | pH (actual) | Buprenorphine detected* (mg/ml) |
| --- | --- | --- | --- |
| 036 | 0 | 3 (3.1) | 13.7 |
| 040 | 12.5 | 3 (2.9) | 13.1 |
| 041 | 25 | 3 (2.7) | 13.9 |
| 042 | 37.5 | 3 (3.0) | 13.9 |
| 043 | 50 | 3 (3.2) | 12.3 |
| 037 | 0 | 4 (3.9) | 16.4 |
| 045 | 12.5 | 4 (3.8) | 16.0 |
| 046 | 25 | 4 (3.9) | 15.6 |
| 047 | 37.5 | 4 (4.0) | 15.6 |
| 048 | 50 | 4 (4.0) | 14.3 |
| 038 | 0 | 5 (4.9) | 4.4 |
| 050 | 12.5 | 5 (5.0) | 5.7 |
| 051 | 25 | 5 (5.0) | 4.4 |
| 052 | 37.5 | 5 (5.1) | 4.4 |
| 053 | 50 | 5 (5.2) | 4.6 |
| 039 | 0 | 6 (5.9) | 1.8 |
| 055 | 12.5 | 6 (5.7) | 1.6 |
| 056 | 25 | 6 (5.8) | 1.7 |
| 057 | 37.5 | 6 (5.7) | 1.7 |
| 058 | 50 | 6 (5.6) | 1.8 |

*Expressed as buprenorphine free base

TABLE 10

Effect of mannitol concentration on the solubility of BPN•HCl in solution containing 20 mg/ml pectin (Slendid 100).

| Batch No. | Mannitol concentration (mg/ml) | pH (actual) | Buprenorphine detected* (mg/ml) |
| --- | --- | --- | --- |
| 036 | 0 | 3 (3.2) | 13.7 |
| 060 | 12.5 | 3 (3.1) | 13 |
| 061 | 25 | 3 (3.1) | 12.3 |
| 062 | 37.5 | 3 (3.0) | 12.4 |
| 063 | 50 | 3 (3.2) | 13.9 |
| 037 | 0 | 4 (3.9) | 16.4 |
| 065 | 12.5 | 4 (4.0) | 16.4 |
| 066 | 25 | 4 (4.0) | 15.8 |
| 067 | 37.5 | 4 (4.0) | 15.7 |
| 068 | 50 | 4 (4.0) | 15.5 |
| 038 | 0 | 5 (4.9) | 4.4 |
| 070 | 12.5 | 5 (5.1) | 4.9 |
| 071 | 25 | 5 (5.2) | 3.9 |
| 072 | 37.5 | 5 (5.1) | 4.6 |
| 073 | 50 | 5 (5.2) | 4.3 |
| 039 | 0 | 6 (5.9) | 1.8 |
| 075 | 12.5 | 6 (5.9) | 2.0 |
| 076 | 25 | 6 (5.6) | 1.9 |
| 077 | 37.5 | 6 (5.6) | 2.4 |
| 078 | 50 | 6 (5.3) | 1.8 |

*Expressed as buprenorphine free base

Negative Control Experiment: Effect of Mixing HM (High Methoxy) Pectin (20 mg/ml Genu (Trade Mark) Pectin [Citrus] Type USP-H) Solution with Calcium The pectins suitable for retaining drugs at mucosal surfaces have a low degree of esterification (also called "low methoxy" or "LM" pectins) and, in aqueous solution, will gel in the presence of ions found in mucosal fluid, especially divalent ions, in particular calcium. As a negative control, a solution of "high methoxy" pectin was prepared and mixed with a solution containing calcium ions.

1. Methods

Buprenorphine hydrochloride (107.5 mg), anhydrous dextrose (1.25 g) and pectin (Genu pectin [citrus] type USP-H; CP Kelco, Lille Skenved, Denmark) (500 mg) were stirred in 18-20 ml water in a 25 ml volumetric flask overnight or until a solution formed. The mixture was then made up to 25 ml with water to give a solution containing 4 mg/ml buprenorphine, 20 mg/ml pectin and 50 mg/ml dextrose and the pH and osmolality were determined. A 20 ml aliquot of the formulation was mixed (under controlled conditions) with 5 ml of a standard calcium chloride solution (9.44 mg/ml $CaCl_2.2H_2O$) before standing for 1 hour at room temperature. The structure, uniformity and clarity of the product were then evaluated.

2. Results

The solution had a pH of 3.3 and an osmolality of 0.35 osmol/kg. An opaque, pale yellow solution was formed when the solution was mixed with 9.44 mg/ml $CaCl_2.2H_2O$. The solution did not gel even when left for 1 hour at room temperature.

EXAMPLE 8

Clinical Study

Unit doses of the intranasal buprenorphine formulations of Examples 1, 3 and 5 (Formulations A to C) and one intravenous commercial buprenorphine formulation (Temgesic-trade mark; Formulation D) were administered to healthy human volunteers. The unit doses administered to the volunteers were as follows:

800 µg buprenorphine hydrochloride, calculated as buprenorphine, of Formulations A, B or C administered intranasally; and a single slow intravenous injection of 400 µg buprenorphine hydrochloride, calculated as buprenorphine, of Formulation D.

The dosing was performed on twelve healthy volunteers using a randomised, complete crossover design. Each dose was separated by, at least, seven days. The volunteers were required to fast overnight prior to dosing. Subjects were admitted to a clinic the evening before each dose of administration and remained in the clinic until blood sample collection for each study day. Blood samples were collected at regular intervals up to 24 hours after each dose administration. The volunteers were discharged from the clinic after completion of all 24 hour study procedures. There was a wash out period of, at least seven days, between each dose.

Figure 2:
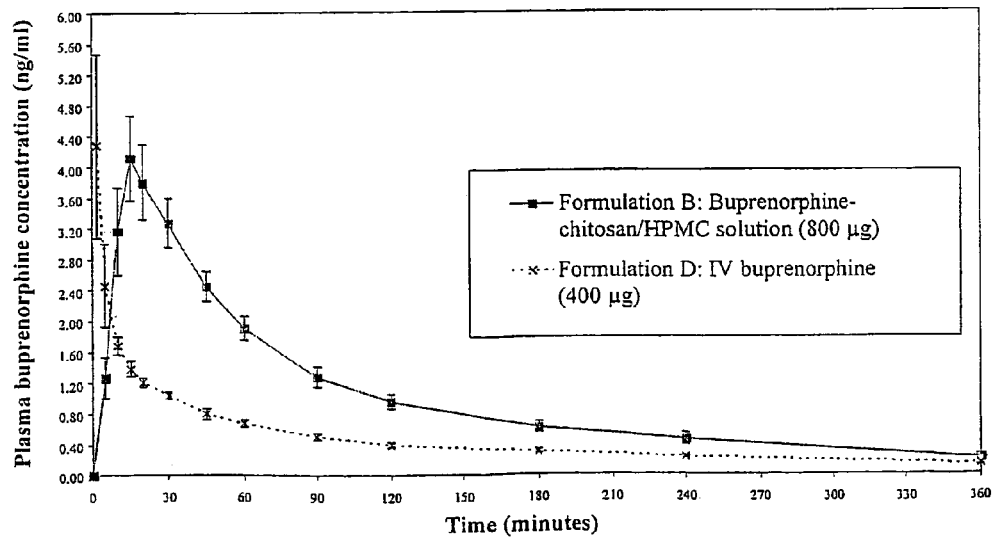
Figure 3:
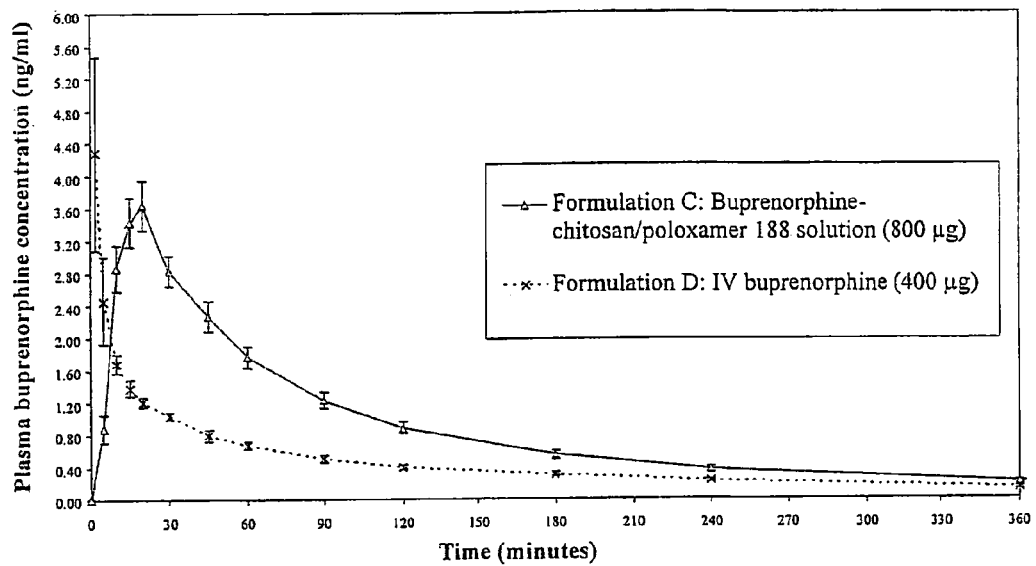

The pharmacokinetics of each dosage regimen were evaluated. The results are shown in FIGS. 1 to 3. All three intranasal solutions showed similar pharmacokinetic profiles. The $C_{ther}$ was reached within 5 to 10 minutes for each formulation and the $C_{max}$ was reached in 20 minutes or less. The data indicated that the initial plasma peak was blunted for the intranasal formulations compared to intravenous administration. That appeared most pronounced for Formulation A. All three intranasal solutions gave high bioavailability (Table 11)

TABLE 11

Comparison of key pharmacokinetic parameters derived from the clinical study data on intranasal buprenorphine with published data on the sublingual tablet and with a dextrose formulation of buprenorphine.

| PK Parameter | Clinical study data Intranasal Buprenorphine | | | (prior art) sublingual Buprenorphine | | (prior art) intranasal Buprenorphine |
|---|---|---|---|---|---|---|
| | 0.8 mg Pectin | 0.8 mg Chitosan/ HPMC | 0.8 mg Chitosan/ Poloxamer | 0.4 mg tablet | 0.8 mg tablet | 0.3 mg dextrose solution |
| $C_{max}$ (ng/ml) | 3.7 | 4.4 | 3.8 | 0.5 | 1.04 | 1.8 |
| $T_{max}$ (min) | 20 | 18 | 20 | 210 | 192 | 31 |
| Bioavailability | 80% | 81% | 72% | | 56% | 48% |

Figure 4:
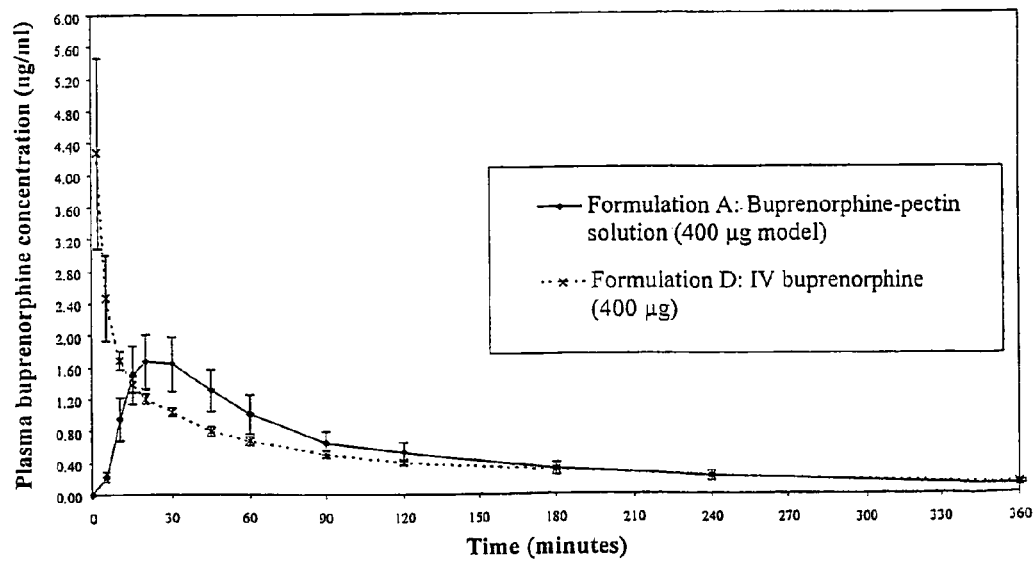
FIG. 4 shows a pharmacokinetic profile for a 400 µg dose of Formulation A. This profile was calculated from the data for the 800 µg dose of Formulation A. The pharmacokinetic profile for the 400 µg dose of Formulation D is also shown for comparison.

A pharmacokinetic profile was computed for a 400 μg intranasal dose of Formulation A, calculated as buprenorphine, from the data for the 800 μg dose of Formulation A. This profile is shown in FIG. 4. FIG. 4 also shows the pharmacokinetic profile for the 400 μg dose of Formulation A that was administered intravenously.

The invention claimed is:

1. An aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%;
    which solution has a pH of from 3 to 4.2, is substantially free from divalent metal ions and gels on the nasal mucosa, and wherein said solution provides a bioavailability of 80% or more of the buprenorphine or physiologically acceptable salt or ester thereof.

2. A solution according to claim 1, wherein the buprenorphine or buprenorphine salt or ester is present in an amount of from 0.5 to 8 mg/ml.

3. A solution according to claim 2, wherein the buprenorphine or buprenorphine salt or ester is present in an amount of from 1 to 6 mg/ml calculated as buprenorphine.

4. A solution according to claim 1, which comprises buprenorphine hydrochloride.

5. A solution according to claim 1, wherein the pectin is present in an amount of from 10 to 30 mg/ml.

6. A solution according to claim 1, wherein the pectin has a degree of esterification of from 10 to 35%.

7. A solution according to claim 1, wherein the pH is from 3.5 to 4.0.

8. A solution according to claim 1, wherein the pH has been adjusted by means of hydrochloric acid.

9. A solution according to claim 1, which comprises a preservative.

10. A solution according to claim 9, which comprises phenylethyl alcohol and propyl hydroxybenzoate as preservatives.

11. A solution according to claim 1, which has an osmolality of from 0.35 to 0.5 osmol/kg.

12. A solution according to claim 1, which contains dextrose as a tonicity adjustment agent.

13. An aqueous solution suitable for intranasal administration, which has a pH of from 3.5 to 4.0, which is substantially free from divalent metal ions and which comprises:
    (a) from 1 to 6 mg/ml of buprenorphine or a physiologically acceptable salt or ester thereof, calculated as buprenorphine,
    (b) from 10 to 40 mg/ml of a pectin which has a degree of esterification from 10 to 35%, and
    (c) dextrose as a tonicity adjustment agent.

14. A process for the preparation of an aqueous solution as defined in claim 1, which process comprises dissolving buprenorphine or a physiologically acceptable salt or ester thereof in water; mixing the resulting solution with a solution in water of a pectin having a degree of esterification of less than 50% such that the mixed solution comprises from 0.1 to 10 mg/ml of buprenorphine or said salt or ester thereof and from 5 to 40 mg/ml of the pectin; and
    adjusting the pH of the solution to a value from 3 to 4.2 if desired.

15. A process according to claim 14, wherein the resulting solution is introduced into a nasal delivery device.

16. A nasal delivery device loaded with a solution as claimed in claim 1.

17. A device according to claim 16, which is a spray device.

18. A method of inducing analgesia in a patient in need thereof, which method comprises intranasally administering an aqueous solution as defined in claim 1.

19. An aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%; which solution has a pH of from 3 to 4.2, is substantially free from divalent metal ions and gels on the nasal mucosa, whereby, on introduction into the nasal cavity of a patient to be treated, the buprenorphine or physiologically acceptable salt or ester thereof is delivered to the bloodstream to produce within 2 to 15 minutes a therapeutic plasma concentration $C_{ther}$ of 0.8 to 5 ng/ml which is maintained for a duration $T_{maint}$ of at least 2 hours, and wherein said solution provides a bioavailability of 80% or more of the buprenorphine or physiologically acceptable salt or ester thereof.

20. An aqueous solution suitable for intranasal administration, which has a pH of from 3.5 to 4.0, which is substantially free from divalent metal ions and which comprises:
    (a) from 1 to 6 mg/ml of buprenorphine or a physiologically acceptable salt or ester thereof, calculated as buprenorphine,
    (b) from 10 to 40 mg/ml of a pectin which has a degree of esterification from 10 to 35%, and
    (c) dextrose as a tonicity adjustment agent, whereby, on introduction into the nasal cavity of a patient to be treated, the buprenorphine or physiologically salt or ester thereof is delivered to the bloodstream to produce within 2 to 15 minutes a therapeutic plasma concentration $C_{ther}$ of 0.8 to 5 ng/ml which is maintained for a duration $T_{maint}$ of at least 2 hours, and wherein said solution provides a bioavailability of 80% or more of the buprenorphine or physiologically acceptable salt or ester thereof.

21. An aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%;

which solution has a pH of from 3 to 4.2, is substantially free from divalent metal ions and gels on the nasal mucosa, wherein said solution provides a peak plasma concentration ($C_{max}$) of the buprenorphine or physiologically acceptable salt or ester thereof in 20 minutes or less ($T_{max}$) on introduction into the nasal cavity of a patient to be treated, and wherein said solution provides a bioavailability of 80% or more of the buprenorphine or physiologically acceptable salt or ester thereof.

22. An aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%;

which solution has a pH of from 3 to 4.2, is substantially free from divalent metal ions and gels on the nasal mucosa, wherein said solution provides a peak plasma concentration ($C_{max}$) of the buprenorphine or physiologically acceptable salt or ester thereof in 10 to 30 minutes ($T_{max}$) on introduction into the nasal cavity of a patient to be treated, and wherein said solution provides a bioavailability of 80% or more of the buprenorphine or physiologically acceptable salt or ester thereof.

23. A solution according to claim 22 wherein the $T_{max}$ is 15 to 25 minutes.

24. A solution according to claim 23 wherein the $T_{max}$ is 15 to 20 minutes.

25. A solution according to claim 22 wherein the $T_{max}$ is 10 to 20 minutes.

26. An aqueous solution suitable for intranasal administration, which comprises from 0.1 to 10 mg/ml of buprenorphine or a physiologically acceptable salt or ester thereof and from 5 to 40 mg/ml of a pectin having a degree of esterification of less than 50%;

which solution has a pH of from 3 to 4.2, is substantially free from divalent metal ions and gels on the nasal mucosa, wherein said solution provides a bioavailability of 80% or more of the buprenorphine or physiologically acceptable salt or ester thereof on introduction into the nasal cavity of a patient to be treated.

\* \* \* \* \*

UNITED STATES PATENT AND TRADEMARK OFFICE
CERTIFICATE OF CORRECTION

| | | |
|---|---|---|
| PATENT NO. | : 7,666,876 B2 | Page 1 of 1 |
| APPLICATION NO. | : 10/508336 | |
| DATED | : February 23, 2010 | |
| INVENTOR(S) | : P. Birch et al. | |

It is certified that error appears in the above-identified patent and that said Letters Patent is hereby corrected as shown below:

On title page delete "(22)" and insert --(22) PCT Filed: March 19, 2003--

Signed and Sealed this

Ninth Day of November, 2010

David J. Kappos
*Director of the United States Patent and Trademark Office*